(12) United States Patent
Glukhovsky et al.

(10) Patent No.: US 8,538,517 B2
(45) Date of Patent: *Sep. 17, 2013

(54) IMPLANT, SYSTEM AND METHOD USING IMPLANTED PASSIVE CONDUCTORS FOR ROUTING ELECTRICAL CURRENT

(75) Inventors: Arkady Glukhovsky, Valencia, CA (US); Yitzhak Zilberman, Valencia, CA (US); Arthur Prochazka, Edmonton, CA (US); Mark Chamberlain, Valencia, CA (US); Ross Davis, Melbourne Beach, FL (US); Joseph Schulman, Santa Clarita, CA (US)

(73) Assignee: Bioness Inc., Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,739

(22) Filed: Sep. 14, 2012

(65) Prior Publication Data
US 2013/0013041 A1    Jan. 10, 2013

Related U.S. Application Data

(63) Continuation of application No. 11/993,393, filed as application No. PCT/US2006/025146 on Jun. 28, 2006, now Pat. No. 8,332,029.

(60) Provisional application No. 60/694,822, filed on Jun. 28, 2005, provisional application No. 60/703,117, filed on Jul. 27, 2005, provisional application No. 60/784,713, filed on Mar. 21, 2006.

(51) Int. Cl.
*A61N 1/00* (2006.01)

(52) U.S. Cl.
USPC ............................................................ 607/2

(58) Field of Classification Search
USPC ...................... 607/2, 3, 41, 48, 115; 606/129
See application file for complete search history.

(56) References Cited

U.S. PATENT DOCUMENTS 3,204,637 A    9/1965   Frank et al.
3,426,748 A    2/1969   Bowers
(Continued)

FOREIGN PATENT DOCUMENTS

CA    2484310    11/2003
EP    0862925     9/1998
(Continued)

OTHER PUBLICATIONS

Office Action for U.S. Appl. No. 11/867,454, mailed Mar. 2, 2011.
(Continued)

*Primary Examiner* — George Manuel
*Assistant Examiner* — Robert N Wieland

(57) ABSTRACT

The present invention provides improvements to an implant, system and method using passive electrical conductors which route electrical current to either external or implanted electrical devices, to multiple target body tissues and to selective target body tissues. The passive electrical conductor extends from subcutaneous tissue located below either a surface cathodic electrode or a surface anodic electrode a) to a target tissue to route electrical signals from the target body tissue to devices external to the body; b) to implanted electrical devices to deliver electrical current to such devices, or c) to multiple target body tissues or to selective target body tissues to stimulate the target body tissues. The conductor has specialized ends for achieving such purposes.

20 Claims, 15 Drawing Sheets

(56) References Cited

U.S. PATENT DOCUMENTS

| | | |
|---|---|---|
| 3,774,618 A | 11/1973 | Avery |
| 3,835,864 A | 9/1974 | Rasor et al. |
| 3,964,470 A | 6/1976 | Trombley |
| 3,995,644 A | 12/1976 | Parsons |
| 4,102,344 A | 7/1978 | Conway et al. |
| 4,323,999 A | 4/1982 | Yoshizawa et al. |
| 4,417,888 A | 11/1983 | Cosentino et al. |
| 4,419,995 A | 12/1983 | Hochmair et al. |
| 4,793,353 A | 12/1988 | Borkan |
| 4,922,927 A | 5/1990 | Fine et al. |
| 4,987,897 A | 1/1991 | Funke |
| 5,080,099 A | 1/1992 | Way et al. |
| 5,098,397 A | 3/1992 | Svensson et al. |
| 5,325,870 A | 7/1994 | Kroll et al. |
| 5,330,516 A | 7/1994 | Nathan |
| 5,356,428 A | 10/1994 | Way |
| 5,397,338 A * | 3/1995 | Grey et al. ............ 607/115 |
| 5,441,518 A | 8/1995 | Adams et al. |
| 5,441,527 A | 8/1995 | Erickson et al. |
| 5,443,065 A | 8/1995 | Berghoff et al. |
| 5,465,715 A | 11/1995 | Lyons |
| RE35,129 E | 12/1995 | Pethica et al. |
| 5,531,782 A | 7/1996 | Kroll et al. |
| 5,545,191 A | 8/1996 | Mann et al. |
| 5,562,707 A | 10/1996 | Prochazka et al. |
| 5,571,148 A | 11/1996 | Loeb et al. |
| 5,674,253 A | 10/1997 | Adams et al. |
| 5,766,231 A | 6/1998 | Erickson et al. |
| 5,776,178 A | 7/1998 | Pohndorf et al. |
| 5,782,645 A | 7/1998 | Stobie et al. |
| 5,796,827 A | 8/1998 | Coppersmith et al. |
| 5,807,397 A | 9/1998 | Barreras |
| 5,843,132 A | 12/1998 | Ilvento |
| 5,914,701 A | 6/1999 | Gersheneld et al. |
| 5,916,244 A | 6/1999 | Walters |
| 5,948,006 A | 9/1999 | Mann |
| 6,006,122 A | 12/1999 | Smits |
| 6,076,016 A | 6/2000 | Feierbach |
| 6,214,032 B1 | 4/2001 | Loeb et al. |
| 6,233,488 B1 | 5/2001 | Hess |
| 6,259,952 B1 | 7/2001 | Sluijter et al. |
| 6,266,567 B1 | 7/2001 | Ishikawa et al. |
| 6,292,699 B1 | 9/2001 | Simon et al. |
| 6,351,674 B2 | 2/2002 | Silverstone |
| 6,366,814 B1 | 4/2002 | Boveja et al. |
| 6,393,323 B1 | 5/2002 | Sawan |
| 6,415,184 B1 | 7/2002 | Ishikawa et al. |
| 6,438,428 B1 | 8/2002 | Axelgaard et al. |
| 6,505,074 B2 | 1/2003 | Boveja et al. |
| 6,505,082 B1 | 1/2003 | Scheiner et al. |
| 6,564,102 B1 | 5/2003 | Boveja |
| 6,668,191 B1 | 12/2003 | Boveja |
| 6,725,096 B2 | 4/2004 | Chinn et al. |
| 6,735,474 B1 | 5/2004 | Loeb et al. |
| 6,735,475 B1 | 5/2004 | Whitehurst et al. |
| 6,754,472 B1 | 6/2004 | Williams et al. |
| 6,829,508 B2 | 12/2004 | Schulman et al. |
| 6,840,919 B1 | 1/2005 | Håkansson |
| 6,847,844 B2 | 1/2005 | Sun et al. |
| 6,879,859 B1 | 4/2005 | Boveja |
| 6,892,098 B2 | 5/2005 | Ayal et al. |
| 6,896,675 B2 | 5/2005 | Leung et al. |
| 6,928,320 B2 | 8/2005 | King |
| 6,941,171 B2 | 9/2005 | Mann et al. |
| 6,961,623 B2 | 11/2005 | Prochazka |
| 7,013,179 B2 | 3/2006 | Carter et al. |
| 7,047,071 B2 | 5/2006 | Wagner et al. |
| 7,146,210 B2 | 12/2006 | Palti |
| 7,162,303 B2 | 1/2007 | Levin et al. |
| 7,324,853 B2 | 1/2008 | Ayal et al. |
| 7,389,145 B2 | 6/2008 | Kilgore et al. |
| 7,415,309 B2 | 8/2008 | McIntyre |
| 7,502,652 B2 | 3/2009 | Gaunt et al. |
| 7,536,226 B2 | 5/2009 | Williams et al. |
| 8,332,029 B2 | 12/2012 | Glukhovsky et al. |
| 2001/0002441 A1 | 5/2001 | Boveja |
| 2001/0047167 A1 | 11/2001 | Heggeness |
| 2002/0055779 A1 | 5/2002 | Andrews |
| 2002/0077831 A1 | 6/2002 | Numa |
| 2002/0111663 A1 | 8/2002 | Dahl et al. |
| 2003/0028232 A1 | 2/2003 | Camps et al. |
| 2003/0078642 A1 | 4/2003 | Malaney et al. |
| 2003/0139794 A1 | 7/2003 | Jenney et al. |
| 2003/0171792 A1 | 9/2003 | Zarinetchi et al. |
| 2003/0199807 A1 | 10/2003 | Dent et al. |
| 2003/0212395 A1 | 11/2003 | Woloszko et al. |
| 2003/0212440 A1 | 11/2003 | Boveja |
| 2003/0236557 A1 | 12/2003 | Whitehurst et al. |
| 2004/0049235 A1 | 3/2004 | Deno et al. |
| 2004/0176804 A1 | 9/2004 | Palti |
| 2004/0220641 A1 | 11/2004 | Wagner et al. |
| 2005/0070970 A1 | 3/2005 | Knudson et al. |
| 2005/0136385 A1 | 6/2005 | Mann et al. |
| 2006/0064140 A1 | 3/2006 | Whitehurst et al. |
| 2006/0184211 A1 | 8/2006 | Gaunt et al. |
| 2006/0206165 A1 | 9/2006 | Jaax et al. |
| 2006/0271118 A1 | 11/2006 | Libbus et al. |
| 2008/0004676 A1 | 1/2008 | Osypka et al. |
| 2008/0046053 A1 | 2/2008 | Wagner et al. |
| 2008/0243216 A1 | 10/2008 | Zilberman et al. |
| 2009/0054952 A1 | 2/2009 | Glukhovsky et al. |
| 2009/0149917 A1 | 6/2009 | Whitehurst et al. |
| 2009/0222053 A1 | 9/2009 | Gaunt et al. |
| 2009/0326602 A1 | 12/2009 | Glukhovsky et al. |
| 2010/0016929 A1 | 1/2010 | Prochazka |
| 2010/0076533 A1 | 3/2010 | Dar et al. |
| 2011/0282412 A1 | 11/2011 | Glukhovsky et al. |

FOREIGN PATENT DOCUMENTS

| | | |
|---|---|---|
| JP | 62-286471 | 12/1987 |
| JP | 07-308392 | 11/1995 |
| JP | 10-509901 | 9/1998 |
| JP | 2003-501207 | 1/2003 |
| WO | WO 95/10323 | 4/1995 |
| WO | WO 00/57950 | 10/2000 |
| WO | WO 01/03768 | 1/2001 |
| WO | WO 2004/052450 | 6/2004 |
| WO | WO 2005/007120 | 1/2005 |
| WO | WO 2005/011541 | 2/2005 |
| WO | WO 2005/037367 | 4/2005 |
| WO | WO 2005/070494 | 8/2005 |
| WO | WO 2006/101917 | 9/2006 |
| WO | WO 2006/113654 | 10/2006 |
| WO | WO 2006/113801 | 10/2006 |
| WO | WO 2007/002741 | 1/2007 |
| WO | WO 2007/008906 | 1/2007 |
| WO | WO 2007/082382 | 7/2007 |
| WO | WO 2008/140242 | 11/2008 |
| WO | WO 2009/058258 | 5/2009 |

OTHER PUBLICATIONS

Final Office Action for U.S. Appl. No. 11/867,454, mailed Jun. 27, 2011.
Final Office Action for U.S. Appl. No. 11/867,454, mailed Oct. 10, 2012.
Examination Report for Australian Patent Application No. 2006261666, mailed Aug. 5, 2010.
Response to Examination Report for Australian Patent Application No. 2006261666, dated May 11, 2011.
Notice of Reasons for Rejection for Japanese Patent Application No. 2008-519515, mailed Sep. 22, 2011.
Decision of Rejection for Japanese Patent Application No. 2008-519515, mailed May 9, 2012.
Notice of Reasons for Rejection for Japanese Patent Application No. 2008-519515, mailed Oct. 10, 2012.
Office Action for U.S. Appl. No. 11/993,393, mailed Nov. 2, 2011.
Office Action for U.S. Appl. No. 11/993,393, mailed Mar. 6, 2012.
International Search Report for International Application No. PCT/US2006/025146, mailed Dec. 12, 2006.
Examiner's Report for Australian Application No. 2011213849, dated Feb. 1, 2012.

Office Action for U.S. Appl. No. 12/147,937, mailed Feb. 2, 2012.
Office Action for U.S. Appl. No. 12/147,937, mailed Oct. 15, 2012.
Supplementary European Search Report for European Application No. EP 09770922.4, mailed Jan. 5, 2012.
Office Action for U.S. Appl. No. 13/000,840, mailed Oct. 9, 2012.
International Search Report and Written Opinion for International Application No. PCT/US2009/048419, mailed Aug. 18, 2009.
Office Action for European Patent Application EP 05700290.9, mailed Jun. 16, 2009.
Partial Translation of Office Action for Japanese Patent Application No. JP 2004-543869, dated May 26, 2009.
Supplementary European Search Report for European Patent Application EP 05700290.9, mailed Jan. 27, 2009.
Supplementary European Search Report for European Patent Application EP 07701705.1, mailed Jun. 7, 2010.
Office Action for U.S. Appl. No. 12/400,202, mailed Aug. 8, 2012.
International Search Report and Written Opinion for International Application No. PCT/CA2010/001487, mailed Jan. 18, 2011.
Abel-Gawad, M. et. al., "Reduction of bladder outlet resistance by selective stimulation of the ventral sacral root using high frequency blockage: a chronic study in spinal cord transected dogs," Journal of Urology, vol. 166 (2001), pp. 728-733.
Ade-Hall, R. et al., "Botulinum toxin type A in the treatment of lower limb spasticity in cerebral palsy (Review)," The Cochrane Library (2009), Issue 3, 19 pages.
Amis, A. et al., "Relative Displacements in Muscle and Tendon During Human Arm Movements," J. Physiol. (1987), vol. 389, pp. 37-44.
Apkarian, J. A. et al., "Stretch reflex inhibition using electrical stimulation in normal subjects and subjects with spasticity," Journal of Biomedical Engineering, vol. 13 (1991), pp. 67-73.
Ashkan, K. et al., "Deep brain stimulation of the subthalamic nucleus in Parkinson's disease 1993-2003: where are we 10 years on?," Br J. Neurosurg, vol. 18 (2004), pp. 19-34.
Benabid, A. L. et al., "Combined (Thalamotomy and stimulation) stereotactic surgery of the VIM thalamic nucleus for bilateral Parkinson disease," Applied Neurophysiology, vol. 50 (1987), pp. 344-346.
Bhadra, N. et al., "High-frequency electrical conduction block of mammalian peripheral motor nerve," Muscle & Nerve (Epub ahead of Dec. 2005 print) (2005), pp. 782-790.
Bhadra, N. et al., "Direct Current Electrical Conduction Block of Peripheral Nerve. IEEE Transactions on Neural Systems and Rehabilitation Engineering," vol. 12, No. 3 (Sep. 2004), pp. 313-324.
Brindley, G. S. et al., "Sacral anterior root stimulators for bladder control in paraplegia," Paraplegia, vol. 20 (1982), pp. 365-381.
Broseta, J. et al., "High-frequency cervical spinal cord stimulation in spasticity and motor disorders," Acta Neurochir Suppl (Wien), vol. 39 (1987), pp. 106-111.
Cattell, M. et al., "The 'Inhibitory' Effect of High-Frequency Stimulation and the Excitation State of Nerve," Department of Physiology, Unversity College, London (Nov. 1934), pp. 407-415.
Filali, M. et al., "Stimulation-induced inhibition of neuronal firing in human subthalamic nucleus," Exp Brain Res, vol. 156(3) (2004), pp. 274-281.
Gans, L. et al., "The Stimulus Router: A Novel Means of Directing Current From Surface Electrodes to Nerves," 10th Annual Conference of the International FES Society (Jul. 2005), Montreal, Canada, pp. 21-23.
Gans et al., "The Stimulus Router: A Novel Means of Directing Current From Surface Electrodes to Nerves," 10th Annual Conference of the International FES Society (Jul. 2005), Montreal, Canada, Display Poster.
Glenn, W. W. et al., "Radiofrequency-controlled catheter pacemaker, Clinical application," New England Journal of Medicine, vol. 275 (1966), pp. 137-140.
Grill, W. M., Jr. et al., "Quantification of recruitment properties of multiple contact cuff electrodes," IEEE Trans. Rehabil. Eng., vol. 4(2) (1996), pp. 49-62.
Groen, J. et al., "Neuromodulation techniques in the treatment of the overactive bladder," BJU Int, vol. 87(8) (2001), pp. 723-731.

Handa, Y. et al., "Application of functional electrical stimulation to the paralyzed extremities," Neurologia Medico-Chirurgica, vol. 38 (1998), pp. 784-788.
Haugland, M. et al., "Interfacing the body's own sensing receptors into neural prosthesis devices," Technology Health Care, vol. 7 (1999), pp. 393-399.
"Innovative Medical Devices for Neuro-Technologies," NeuroTECH, [online] [Retrieved on Sep. 21, 2007] Retrieved from the Internet: <URL: http://www.neurotech.be/Prod_cuffelectrode.htm>.
Jankovic, J. et al., "Outcome after Stereotactic Thalamotomy for Parkinsonian, Essential, and Other Types of Tremor," Neurosurgery Online [online] [retrieved on May 21, 2009] Retrieved from the Internet: <URL:http://www.ovidsp.tx.ovid.com/spa/ovidweb.cgi?&S=AACMFPFHBADDKOHCNCFLGDMJJ...I> 9 pages.
Kilgore, K. L. et al., "Chapter 6.2: Upper and lower extremity motor neuroprostheses," Horch, K.W. and Dhillon, G.S., ed., Neuroprosthetics. Theory and Practice, vol. 2 World Scientific, New Jersey (2004), pp. 844-877.
Kilgore, K. L. et al., "Block of Nerve Conduction Using High Frequency Alternating Current," $9^{th}$ Annual Conference of the International FES Society, Sep. 2004, Bournemouth, UK (2004).
Kralj, A. R. et al. "Functional Electrical Stimulation: Standing and Walking after Spinal Cord Injury," CRC Press, Boca Raton, FL (1989), pp. 1-15.
Landau, B. et al., "Neuromodulation techniques for medically refractory chronic pain," Annu Rev Med vol. 44 (1993), pp. 279-287.
Marsolais et al., "Implantation techniques and experience with percutaneous intramuscular electrodes in the lower extremities," Journal of Rehabilitation Research and Development, Veterans Administration, vol. 3, No. 3, pp. 1-8.
Masini et al., "Activated Pyrolytic Carbon Tip Pacing Leads: An Alternative to Steriod-Eluting Pacing Leads?" Pacing and Clinical Electrophysiology, vol. 19, No. 11 (Nov. 1996), pp. 1832-1835.
McCreery, D. et al., "Charge Density and Charge Per Phase as Cofactors in Neural Injury Induced by Electrical Stimulation," IEEE Transactions on Biomedical Engineering, vol. 37, No. 10 (Oct. 1990), pp. 996-1001.
Melzack et al., "Pain Mechanisms: A New Theory," Science, vol. 150 (Nov. 19, 1965), No. 3699, pp. 971-979.
Merrill, D. et al., "Electrical stimulation of excitable tissue: design of efficacious and safe protocols," Journal of Neuroscience Methods vol. 141 (2005), pp. 171-198.
Peckham et al., "Restoration of key grip and release in the C6 tetraplegic patient through functional electrical stimulation," The Journal of Hand Surgery, vol. 5, No. 5 (Sep. 1980), pp. 462-469.
Peckham, P. H. et al., "Implantable Neuroprosthesis Research G Efficacy of an implanted neuroprosthesis for restoring hand grasp in tetraplegia: a multicenter study," Archives of Physical Medicine & Rehabilitation vol. 82 (2001), pp. 1380-1388.
Prochazka, A. et al., "The bionic glove: an electrical stimulator garment that provides controlled grasp and hand opening in quadriplegia," Arch. Phys. Med. Rehabil. vol. 78 (1997), pp. 608-614.
Prochazka et al., "Clinical experience with reinforced, anchored intramuscular electrodes for functional neuromuscular stimulation," Journal of Neuroscience Methods, vol. 42 (1992), pp. 175-184.
Scheiner, A. et al., "Imbalanced Biphasic Electrical Stimulation: Muscle Tissue Damage," Annals of Biomedical Engineering (1990), vol. 18, pp. 407-425.
Shaker, H. et al., "Sacral root neuromodulation in the Treatment of Various Voiding and Storage Problems," International Urogynecology Journal vol. 10 (1999), pp. 336-343.
Shaker, H. S. et al., "Reduction of bladder outlet resistance by selective sacral root stimulation using high-frequency blockade in dogs: an acute study," J Urol 160 (3 Pt 1) (1997), pp. 901-907.
Skold, C. et al., "Spasticity After Traumatic Spinal Cord Injury: Nature, Severity, and Location," Arch Phys Med Rehabil, vol. 80 (Dec. 1999), pp. 1548-1557.
Solomonow, M. et al., "Control of muscle contractile force through indirect high-frequency stimulation," Am J Phys Med, vol. 62 (1983), pp. 71-82.

Strojnik, P. et al., "Treatment of drop foot using an implantable peroneal underknee stimulator," Scandanavian J. of Rehabil. Med., vol. 19 (1987), pp. 37-43.

Stoykov et al., "Recording Intramuscular EMG Signals Using Surface Electrodes, 2005 IEEE 9th International Conference on Rehabilitation Robotics," Jun. 28-Jul. 1, 2005, Chicago, IL, pp. 291-294.

Tagusari et al., "Fine Trabecularized Carbon: Ideal Material and Texture for Percutaneous Device System of Permanent Left Ventricular Assist Device. Artificial Organs," vol. 22, No. 6 (Jun. 1998), pp. 481-487.

Tai, C. et al., "Block of external urethral sphincter contradiction by high frequency electrical stimulation of pudendal nerve," J Urol, vol. 172 (5 Pt 1) (2004), pp. 2069-2072.

Tai, C. et al., "Response of external urethral sphincter to high frequency biphasic electrical stimulation of pudendal nerve," J Urol, vol. 174(2) (2005), pp. 782-786.

Tai, C. et al., "Voiding Reflex in Chronic Spinal Cord Injured Cats Induced by Stimulating and Blocking Pudendal Nerves," Department of Pharmacology, University of Pittsburgh (2007), Neurourology and Urodynamics 26, pp. 879-886.

Van Heeckeren, D.W. et al., "Electrophrenic respiration by radiofrequency induction," Journal of Thoracic & Cardiovascular Surgery, vol. 52 (1966), pp. 655-665.

Vodovnik, L., "Therapeutic effects of functional electrical stimulation of extremities," Medical and Biological Engineering & Computing, vol. 19 (1981), pp. 470-478.

Walker, J. et al., "Fundamentals of Physics," New Jersey, Hoboken, (2007), pp. 791-817.

Waltz, J. M., "Spinal cord stimulation: a quarter century of development and investigation. A review of its development and effectiveness in 1,336 cases," Stereotactic & Functional Neurosurgery, vol. 69 (1997), pp. 288-299.

Whitwam, J. G. et al., "The Use of Direct Current to Cause Selective Block of Large Fibres in Peripheral Nerves," Br. J. Anaesth. (1975), vol. 47, pp. 1123-1133.

Woo, R., "Spasticity: Orthopedic Perspective," (2001) Special Article, Journal of Child Neurology, vol. 16, No. 1, pp. 47-53.

Yu, D. T. et al., "Percutaneous intramuscular neuromuscular electric stimulation for the treatment of shoulder subluxation and pain in patients with chronic hemiplegia: a pilot study," Arch Phys Med Rehabil, vol. 82 (1997), pp. 20-25.

Office Action for Canadian Application No. 2,608,397, dated Jan. 25, 2013.

Office Action for Japanese Patent Application No. 2011-281270, mailed Jun. 5, 2013.

Office Action for Japanese Application No. 2011-516572, mailed Jun. 21, 2013.

* cited by examiner

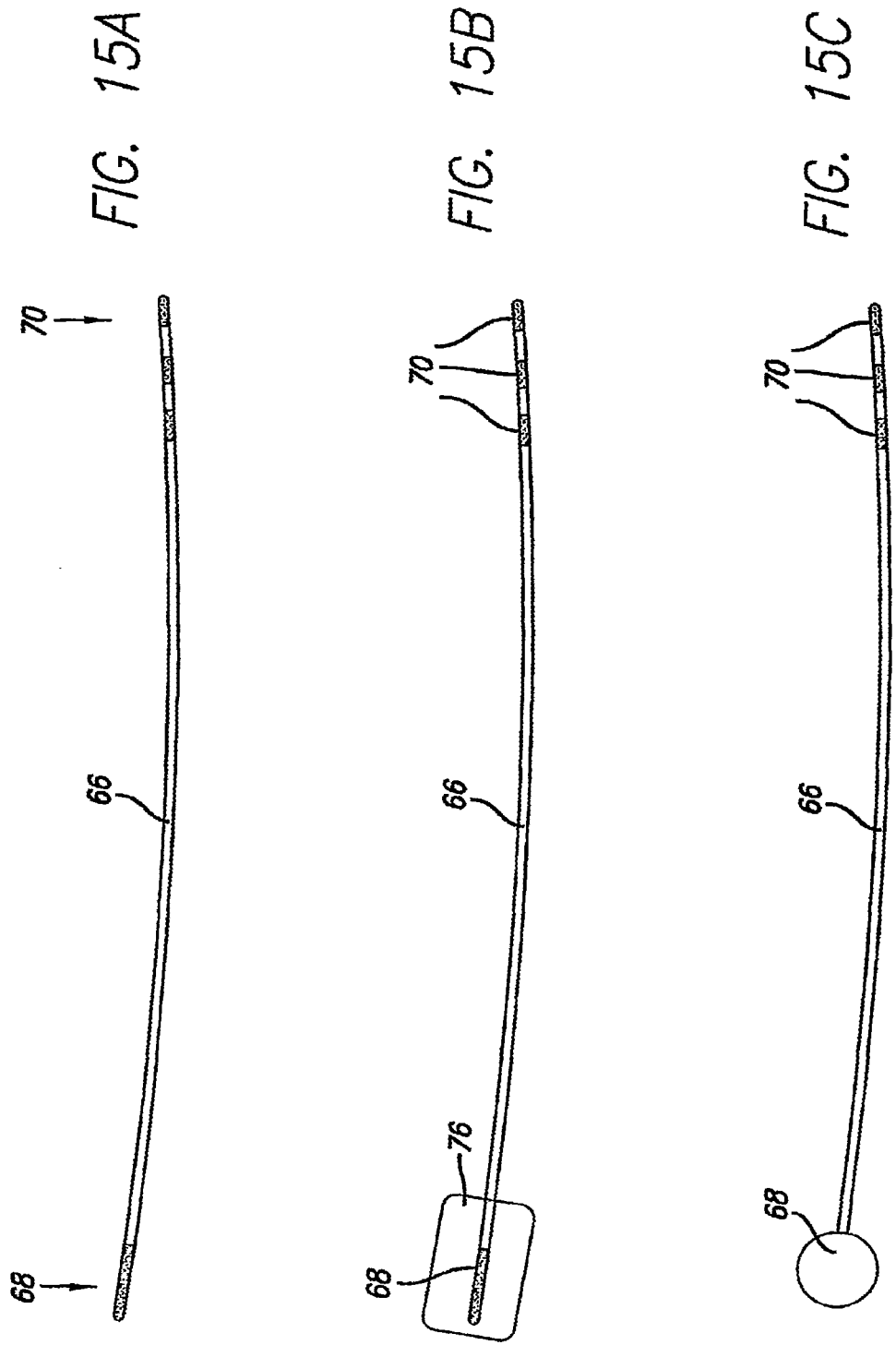

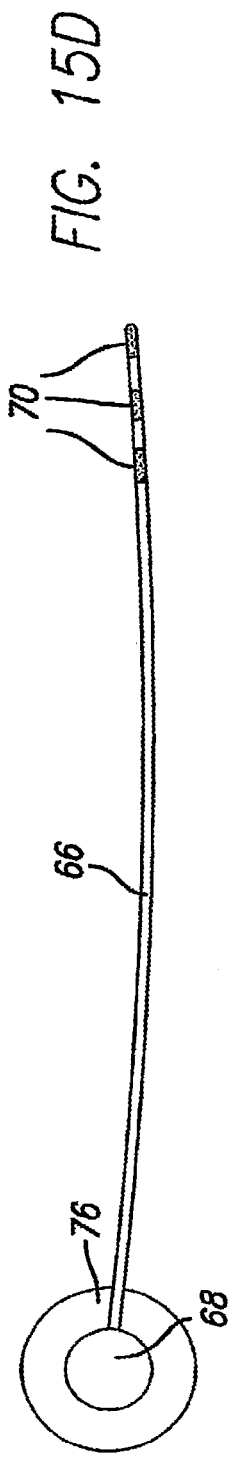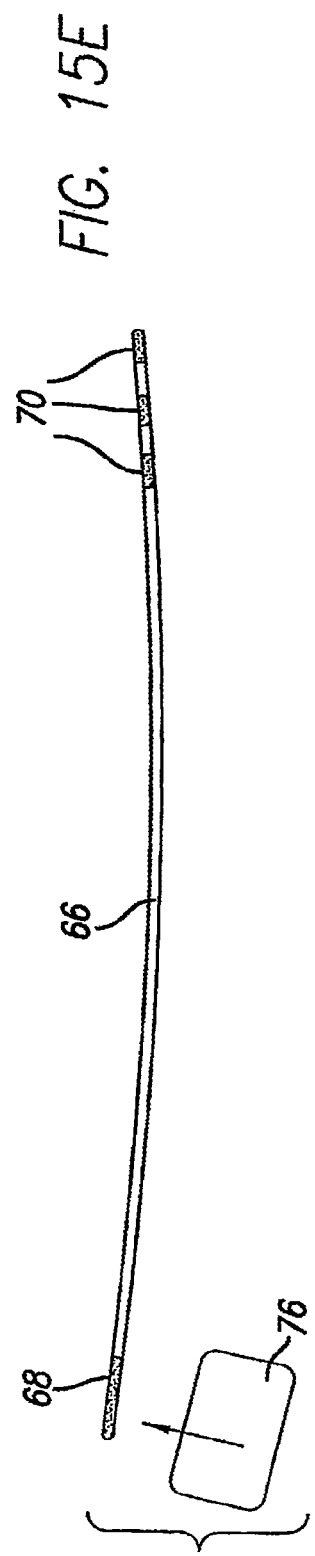

IMPLANT, SYSTEM AND METHOD USING IMPLANTED PASSIVE CONDUCTORS FOR ROUTING ELECTRICAL CURRENT

CROSS-REFERENCE TO RELATED APPLICATIONS

This application is a continuation of and claims priority to U.S. application Ser. No. 11/993,393, which is the U.S. national phase application of International Application No. PCT/US2006/025146, filed Jun. 28, 2006, which claims the benefit of priority from U.S. Provisional Application Ser. Nos. 60/784,713, filed Mar. 21, 2006; 60/703,117, filed Jul. 27, 2005; and 60/694,822, filed Jun. 28, 2005.

FIELD OF THE INVENTION

The present invention relates to improvements to an implant, system and method using passive electrical conductors which route electrical current to either external or implanted devices, to multiple target body tissues and to selective target body tissues.

BACKGROUND OF THE INVENTION

Electrical stimulation of body tissues and nerves is widely used for various indications. Several approaches are known which deliver electrical stimulation to the targeted body area or organ. Some approaches require focused delivery of the stimulation, while others require less targeted stimulation.

Transcutaneous electrical nerve stimulation (commonly referred to as TENS) involves providing electrical signals through the skin for stimulating nerves by attaching electrodes to the skin surface. TENS is advantageous in being non-invasive. However, its effectiveness is questionable since the delivered stimulation is not focused and only a small fraction of the electrical signals delivered through the skin is used effectively.

The electrodes attached to the skin surface cannot select specific body areas, for example particular muscles or deeper muscle tissue. TENS is generally limited to pain relief. However, since the stimulation can be sensed by receptors in the skin, TENS can cause discomfort due to stimulation-induced pain.

Alternatively, percutaneous stimulation can be used to deliver targeted, effective stimulation without activating the skin receptors. A lead is implanted in bodily tissues and led through the skin for connection to an external stimulator. Electrical signals are delivered through the lead to the bodily tissues. However, percutaneous stimulation is not widely practiced since percutaneous leads are unaesthetic and unhygienic, providing a conduit for infection.

Miniature implantable stimulators, for example, the RF BION® device (Advanced Bionics Corporation, California, USA) deliver focused stimulation, while not violating skin integrity. The implanted stimulator can be connected to an implanted lead to position the stimulator close to the skin, while delivering stimulation to deeper body areas. The miniature implanted stimulator requires the delivery of energy from outside the body, which is usually accomplished by an external coil in proximity to the skin to generate a low-frequency magnetic field. A disadvantage of the RF BION® device is the necessity for an external coil. The battery-powered BION® stimulator (Advanced Bionics Corporation) avoids this problem. The BION® stimulator is a miniature implantable stimulator containing a miniature rechargeable battery. The battery can be charged wirelessly using a charging coil, with a relatively short charging time. However, such implantable stimulators are not generally desirable due to their expense.

A system which overcomes the above problems of the current techniques is the "router system" as described in International Publication No. WO 2005/070494 A1 to Prochazka, published Aug. 4, 2005 and claiming priority from U.S. Provisional Patent Application No. 60/538,618 filed Jan. 22, 2004 (Neural Prosthesis Program Meeting, NIH Meeting, November 2004; Gan et al., 2005). The router system is based on a passive electrical conductor (for example, a lead) which extends from subcutaneous tissue located below a surface cathodic electrode to the target body tissue. The electrical conductor has a pick-up end for allowing the electrical current to flow through the conductor, and a stimulating end for delivering electrical current to the target body tissue. A surface anodic electrode is also positioned on the skin. Advantageously, the router system applies sub-sensational levels of transcutaneous stimulation, thereby avoiding stimulation-induced pain. Importantly, focused delivery of the stimulation to the target body tissue is achieved via the passive electrical conductor. Due to such significant advantages, further developments of the router system are desirable.

SUMMARY OF THE INVENTION

The present invention relates to improvements to an implant, system and method using passive electrical conductors which route electrical current to either external or implanted electrical devices, to multiple target body tissues and to selective target body tissues.

In a broad aspect, there is provided a method for selectively and electrically stimulating a target body tissue in a subject comprising the steps of:

a) providing surface cathodic and anodic electrodes for making electrical contact with the subject's skin;

b) providing an implant to act as a conductive pathway for at least a portion of the electrical current flowing between the surface cathodic and anodic electrodes positioned in spaced relationship on the subject's skin and transmitting the portion of the electrical current to the target body tissue, the implant comprising a passive electrical conductor of sufficient length to extend, once implanted, from subcutaneous tissue located below either or both of the surface cathodic electrode or the surface anodic electrode to the target body tissue, the electrical conductor having a pick-up end and a stimulating end, and being insulated between its ends, the pick-up end having a plurality of conductive pick up electrodes and the stimulating end having a plurality of conductive stimulating electrodes, and each of the conductive pick-up electrodes being electrically connected with one or more corresponding conductive stimulating electrodes, such that positioning of either or both of the surface cathodic electrode or the surface anodic electrode over one of the conductive pick-up electrodes causes the portion of the electrical current to be transmitted to the one or more corresponding conductive stimulating electrodes electrically connected to the one of the conductive pick-up electrodes;

c) implanting the implant entirely under the subject's skin, with the conductive pick-up electrodes positioned in the subcutaneous tissue, the conductive stimulating electrodes positioned in the vicinity of the target body tissue, and one or more of the corresponding conductive stimulating electrodes positioned proximate to the target body tissue;

d) positioning the surface cathodic and anodic electrodes in spaced relationship on the subject's skin, with either or both of the surface cathodic electrode or the surface anodic electrode positioned over the conductive pick-up electrode electrically connected with the one or more corresponding conductive stimulating electrodes which are proximate to the target body tissue, so that the portion of the current is transmitted through the electrical conductor to the one or more corresponding conductive stimulating electrodes for stimulation of the target body tissue; and e) applying direct, pulsatile or alternating electrical current between the surface cathodic electrode and the surface anodic electrode to cause the portion of the electrical current to flow through the implant sufficient to stimulate the target body tissue.

In another aspect, there is provided a system for selectively and electrically stimulating a target body tissue in a subject, comprising:

i) surface cathodic and anodic electrodes for making electrical contact with the subject's skin, and which, when positioned in spaced relationship on the subject's skin, transmit electrical current to subcutaneous tissue located below and between the surface cathodic and anodic electrodes;

ii) a stimulator external to the subject's body, electrically connected to the surface cathodic and anodic electrodes, the stimulator supplying electrical current to the 15 surface cathodic and anodic electrodes; and iii) an implant for picking up a portion of the electrical current flowing between the surface cathodic and anodic electrodes and transmitting the portion of the electrical current to the target body tissue, the implant comprising a passive electrical conductor of sufficient length to extend, once implanted, from subcutaneous tissue located below either or both of the surface cathodic electrode or the surface anodic electrode to the target body tissue, and the electrical conductor having a pick-up end and a stimulating end, and being insulated between its ends, the pick-up end having a plurality of conductive pick-up electrodes and the stimulating end having a plurality of conductive stimulating electrodes, and each of the conductive pick-up electrodes being electrically connected with one or more corresponding conductive stimulating electrodes, such that positioning of either or both of the surface cathodic electrode or the surface anodic electrode over one of the conductive pick-up electrodes causes the portion of the electrical current to be transmitted to the one or more corresponding conductive stimulating electrodes electrically connected with that one of the conductive pick-up electrodes.

In another broad aspect, there is provided a method for delivering electrical current to one or more electrical devices implanted within a subject's body, comprising the steps of:

a) providing surface cathodic and anodic electrodes for making electrical contact with the subject's skin;

b) providing an implant to act as a conductive pathway for at least a portion of the electrical current flowing between surface cathodic and anodic electrodes positioned in spaced relationship on the subject's skin and transmitting the portion of the electrical current to the one or more electrical devices, the implant comprising a passive electrical conductor of sufficient length to extend, once implanted, from the subcutaneous tissue located below either or both of the surface cathodic electrode or the surface anodic electrode to the one or more electrical devices, the electrical conductor having a pick-up end and a delivery end and being insulated between its ends, the pick-up end forming an electrical termination having a sufficient surface area to allow a sufficient portion of the electrical current to flow through the conductor, and the delivery end forming an electrical termination for delivering the portion of electrical current to the one or more electrical devices;

c) providing the one or more electrical devices;

d) implanting the implant entirely under the subject's skin, with the pick-up end positioned in subcutaneous tissue located below either or both the surface cathodic electrode or the surface anodic electrode;

e) implanting the one or more electrical devices entirely under the subject's skin, the one or more electrical devices being positioned along the electrical conductor or formed as the electrical termination of the pick-up end, and the one or more electrical devices being electrically connected to the electrical conductor such that the electrical current is transmitted from the electrical conductor to the one or more electrical devices;

f) positioning the surface cathodic and anodic electrodes in spaced relationship on the subject's skin, with either or both the surface cathodic electrode or the surface anodic electrode positioned over the pick-up end of the electrical conductor so the portion of the current is transmitted through the conductor to the one or more electrical devices, and returns to either the surface cathodic electrode or the surface anodic electrode through body tissues; and g) applying direct, pulsatile or alternating electrical current between the surface cathodic electrode and the surface anodic electrode to cause the portion of the electrical current to flow through the implant sufficient to deliver electrical current to the one or more electrical devices.

In another aspect, there is provided a system for delivering electrical current to one or more electrical devices implanted within a subject's body, comprising:

i) surface cathodic and anodic electrodes for making electrical contact with the subject's skin, and which, when positioned in spaced relationship on the subject's skin, transmit electrical current to subcutaneous tissue located below and between the surface cathodic and anodic electrodes;

ii) a stimulator external to the subject's body, electrically connected to the surface cathodic and anodic electrodes, the stimulator supplying electrical current to the surface cathodic and anodic electrodes;

iii) an implant for picking up a portion of the electrical current flowing between the surface cathodic and anodic electrodes and transmitting that portion of the electrical current to the one or more electrical devices, the implant comprising a passive electrical conductor of sufficient length to extend, once implanted, from subcutaneous tissue located below either or both of the surface cathodic electrode or the surface anodic electrode to the one or more electrical devices, the electrical conductor having a pick-up end and a delivery end and being insulated between its ends, the pick-up end forming an electrical termination having a sufficient surface area to allow a sufficient portion of the electrical current being applied to flow through the conductor, in preference to current flowing through body tissue between the surface cathodic and anodic electrodes, such that the one or more devices are supplied with current, and the delivery end forming an electrical termination with the one or more devices for delivering the portion of electrical current to the one or more devices; and iv) the one or more electrical devices being electrically connected to the electrical conductor such that the electrical current is transmitted from the conductor to the one or more electrical devices.

In another broad aspect, there is provided a method for delivering an electrical signal from a target body tissue to one or more external devices located external to a subject's body, the method comprising the steps of:

a) providing a surface electrode for making electrical contact with the subject's skin;

b) providing an implant to act as a conductive pathway for the electrical signals from the target body tissue, the implant comprising a passive electrical conductor of sufficient length to extend, once implanted, from subcutaneous tissue located below a surface electrode positioned on the subject's skin to the target body tissue, the electrical conductor having a pick-up end and a delivery end and being insulated between its ends, the pick-up end forming an electrical termination having a sufficient surface area to allow the electrical signal from the target body tissue to flow through the conductor, and the delivery end forming an electrical termination for delivering the electrical signal to the one or more external devices;

c) implanting the implant entirely under the subject's skin, with the delivery end positioned in subcutaneous tissue located below the surface electrode, and the pick-up end positioned proximate to the target body tissue; and d) positioning the surface electrode on the subject's skin, with the surface electrode positioned over the delivery end of the electrical conductor, the surface electrode being electrically connected to the one or more external devices such that the electrical signal from the target body tissue is transmitted through the conductor to the one or more external devices.

In another aspect, there is provided a system for delivering electrical signals from a target body tissue to one or more external devices to be located external to a subject's body comprising:

i) at least one surface electrode for making electrical contact with the subject's skin; and ii) an implant for picking up the electrical signal from the target body tissue and transmitting the electrical signal to the one or more external devices, the implant comprising a passive electrical conductor of sufficient length to extend, once implanted, from subcutaneous tissue located below the at least one surface electrode to the target body tissue, the electrical conductor having a pick-up end and a delivery end and being insulated between its ends, the pick-up end forming an electrical termination having a sufficient surface area to allow the electrical signal from the target body tissue to flow through the conductor, and the delivery end forming an electrical termination for delivering the electrical signal to the one or more external devices.

In another broad aspect, there is provided a method for stimulating a plurality of target body tissues comprising the steps of:

a) providing one or more surface cathodic and anodic electrodes for making electrical contact with the subject's body;

b) providing one or more external stimulators, the one or more external stimulators being external to the subject's body, electrically connected to the one or more surface cathodic and anodic electrodes, the stimulator supplying electrical current to the one or more surface cathodic and anodic electrodes;

c) providing a plurality of implants for electrically stimulating a plurality of target body tissues independently or in unison, each implant acting as a conductive pathway for at least a portion of the electrical current flowing between the one or more surface cathodic and anodic electrodes positioned in spaced relationship on the subject's skin and transmitting the portion of the electrical current to the plurality of target body tissues, each implant comprising a passive electrical conductor of sufficient length to extend, once implanted, from subcutaneous tissue located below either the one or more surface cathodic electrodes or the one or more surface anodic electrodes to a plurality of target body tissues, and each electrical conductor having a pick-up end and a stimulating end and being insulated between its ends, the pick-up end forming an electrical termination having a sufficient surface area to allow a sufficient portion of the electrical current to flow through the conductor such that the target body tissue is stimulated, and the stimulating end forming an electrical termination for delivering the portion of electrical current to the target body tissue;

d) implanting the plurality of implants entirely under the subject's skin, with the pick-up ends of the electrical conductors positioned in subcutaneous tissue located below either or both of the one or more surface cathodic electrodes or the one or more surface anodic electrodes, and the stimulating ends positioned proximate to the plurality of target body tissues;

e) positioning the surface cathodic and anodic electrodes in spaced relationship on the subject's skin, with either or both of the surface cathodic electrodes or the surface anodic electrodes positioned over the pick-up ends of the electrical conductors so the portion of the current is transmitted through the conductors to the plurality of target body tissues, so that the current flows through the plurality of target body tissues and returns to either the surface cathodic electrodes or the surface anodic electrodes through body tissues; and f) applying direct, pulsatile or alternating electrical current between the one or more surface cathodic electrodes and anodic electrodes to cause the portion of the electrical current to flow through the plurality of implants sufficient to stimulate the plurality of target body tissues.

In another aspect, there is provided a system for electrically stimulating a plurality of target body tissues in a subject comprising:

i) surface cathodic and anodic electrodes for making electrical contact with the subject's skin, and which, when positioned in spaced relationship on the subject's skin, transmit electrical current to the plurality of target body tissues; ii) a stimulator external to the subject's body, electrically connected to the surface cathodic and anodic electrodes, the stimulator supplying direct, pulsatile, or alternating current to the surface cathodic and anodic electrodes; and iii) a plurality of implants for picking up a portion of the electrical current flowing between the surface cathodic and anodic electrodes and transmitting that portion of the electrical current to the plurality of the target body tissues, each of the plurality of implants comprising a passive electrical conductor of sufficient length to extend, once implanted, from subcutaneous tissue located below either the surface cathodic electrode or the surface anodic electrode to the target body tissue, the electrical conductor having a pick-up end and a stimulating end and being insulated between its ends, the pick-up end forming an electrical termination having a sufficient surface area to allow a sufficient portion of the electrical current being applied to flow through the conductor, in preference to current flowing through body tissue between the surface cathodic and anodic electrodes, such that the target body tissue is stimulated, and the stimulating end forming an electrical termination for delivering the portion of electrical current to the target body tissue.

In general, the terms and phrases used herein have their art-recognized meaning, which can be found by reference to standard texts, journal references and contexts known to those skilled in the art. The following definitions are provided to clarify their specific use in the context of the invention.

"Activating" or "activate" is meant to refer to inducing the conduction or propagation of action potentials or nerve impulses along the axons of the target nerve partially or completely.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Blocking" or "block" is meant to refer to preventing the conduction or propagation of action potentials or nerve impulses along the axons of a target nerve partially or completely.

"Body tissue" is meant to refer to a neural tissue (in the peripheral or central nervous system), a nerve, a muscle (skeletal, respiratory, or cardiac muscle) or an organ, for example, the brain, cochlea, optic nerve, heart, bladder, urethra, kidneys and 30 bones.

"Electrical device" means an device powered by electrical current or which processes electrical signals.

"Electrically connected" means connected in a manner to permit transmission of electrical current.

"Electrical current" is meant to refer to current applied at the surface of the skin that is resistively and capacitively coupled to the implanted passive conductor, which in turn conveys the current to the target body tissue or device.

"Proximate" means a distance sufficiently close to stimulate the target body tissue including direct contact with the target body tissue.

"Stimulate" means stimulating a target nerve to either activate or block the conduction or propagation of action potentials or nerve impulses along the axons of the target nerve partially or completely.

"Subject" means an animal including a human.

"Vicinity" means a distance near the target body tissue but not sufficiently close to stimulate the target body tissue.

When a Markush group or other grouping is used herein, all individual members of the group and all combinations and subcombinations possible of the group are intended to be individually included in the disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of excludes any element, step or ingredient not specified in the claim element. As used herein, "consisting essentially of does not exclude materials or steps that do not materially affect the basis and novel characteristics of the claim. Any recitation herein of the term "comprising," particularly in a description of components of a composition or a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The use of the indefinite article "a" in the claims before an element means that one of the elements is specified, but does not specifically exclude others of the elements being present, unless the context clearly requires that there be one and only one of the elements.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by the preferred embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be further described by way of example only and with reference to the following figures in which similar references are used in different figures to denote similar components, and wherein:

FIG. 15A is a schematic view illustrating a lead having a conductive pick-up electrode and three conductive stimulating electrodes.

FIG. 15B is a schematic view illustrating a lead having a conductive pick-up coil electrode with insulating backing FIG. 15C is a schematic view illustrating a lead having a conductive pick-up circular electrode and three conductive stimulating electrodes.

FIG. 15D is a schematic view illustrating lead having a conductive pick-up circular electrode with insulating backing and three conductive stimulating electrodes.

FIG. 15E is a schematic view illustrating a lead having a conductive pick-up electrode to which insulating backing is attached during implantation.

DESCRIPTION OF THE PREFERRED EMBODIMENT

The present invention broadly relates to improvements of a "router system" as described in International Publication No. WO 2005/070494 A1 to Prochazka (published Aug. 4, 2005 and claiming priority from U.S. Provisional Patent Application No. 60/538,618 filed Jan. 22, 2004), and U.S. patent application Ser. No. 11/337,824 filed Jan. 23, 2006 to Gaunt and Prochazka. These applications describe an implant for electrically stimulating a target body tissue, such as a nerve, in a subject to either activate or block neural impulses depending on the condition to be treated.

Figure 1:
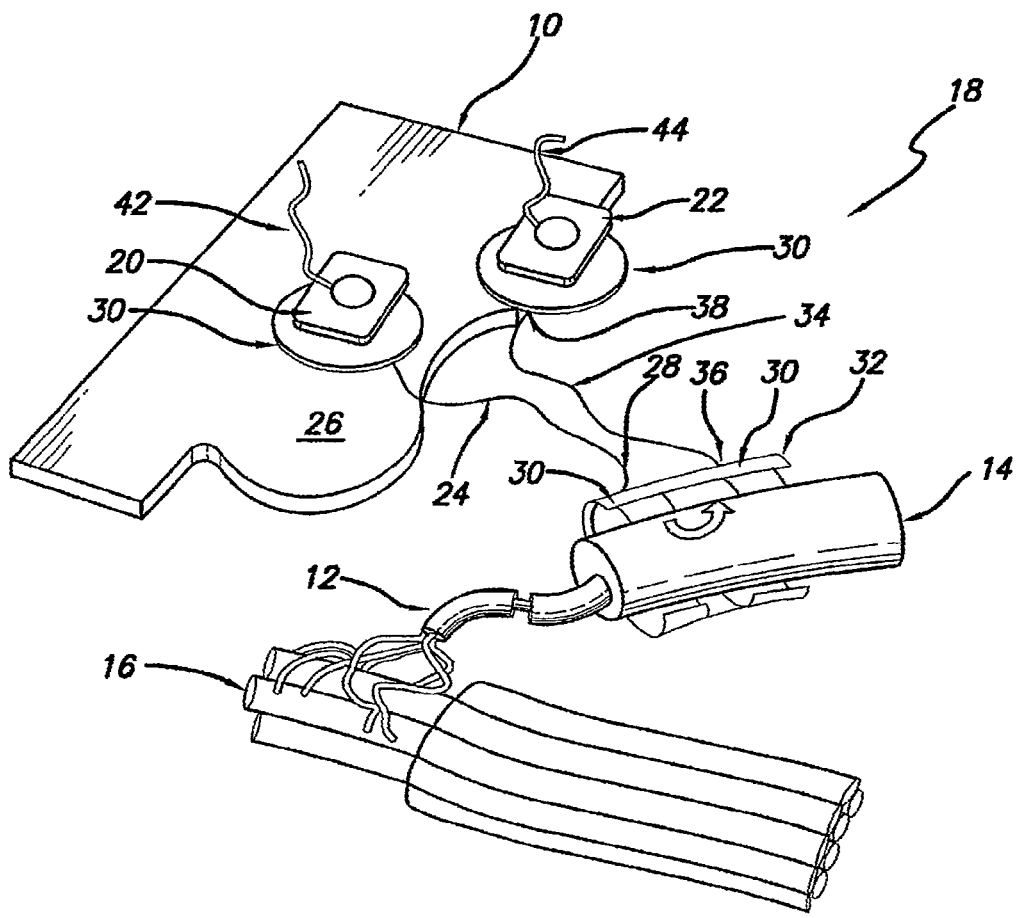
FIG. 1 is a schematic three-dimensional view of the router system of the prior art having an implanted electrical conductor, surface cathodic and anodic electrodes, and an implanted electrical return conductor.

FIG. 1 taken from WO 2005/070494 A1 shows the subject's skin 10, a nerve 12, nerve sheath 14, and a muscle 16. The implant 18 provides a conductive pathway for at least a portion of the electrical current flowing between the surface cathodic and anodic electrodes 20, 22. The implant 18 comprises a passive electrical conductor 24 of sufficient length to extend, once implanted, from subcutaneous tissue located below the surface cathodic electrode 20 to the target body tissue 12. The electrical conductor has a pick-up end 26 and a stimulating end 28, of which one or both form electrical terminations having sufficient surface areas for reducing the electrical impedance of the interface between the pick-up and stimulating ends 26, 28 of the electrical conductor 24 and the surrounding body tissues. The terminations 30 are shown in FIG. 1 in the form of an embracing cuff 32 placed around the nerve 12. An optional electrical return conductor 34 provides a low-impedance conductive pathway from the target body tissue to the surface anodic electrode 22, thereby concentrating the electric field through the target tissue 12. The electrical return conductor 34 has a collecting end 36 and a returning end 38. Cathodic wire 42 and anodic wire 44 are connected to an external stimulator (not shown) to which operating power is provided by a power source (not shown). Once implanted, the implant 18 provides a conductive pathway for at least a portion of the electrical current flowing between the surface cathodic and anodic electrodes 20, 22.

The router system has been described in International Publication No. WO 2005/070494 A1 and U.S. patent application Ser. No. 11/337,824 as beneficial for various conditions in which stimulation to either activate or block neural impulses is required. Such conditions can include movement disorders (e.g., spasticity, hypertonus, rigidity, tremor and/or muscle weakness, Parkinson's disease, dystonia, cerebral palsy), muscular disorders (e.g., muscular dystrophy), incontinence (e.g., urinary bladder disorders), urinary retention, pain (e.g., migraine headaches, neck and back pain, pain resulting from other medical conditions), epilepsy (e.g., generalized and partial seizure disorder), cerebrovascular disorders (e.g., strokes, aneurysms), sleep disorders (e.g., sleep apnea), autonomic disorders (e.g., gastrointestinal disorders, cardiovascular disorders), disorders of vision, hearing and balance, and neuropsychiatric disorders (e.g., depression). The router system may also be used for promoting bone growth (as required, for example, in the healing of a fracture), wound healing or tissue regeneration.

The present invention contemplates use of the router system for specific categories of conditions described in Table 1:

TABLE 1

Summary of Conditions

| Category of Condition | Examples of Specific Conditions |
|---|---|
| Functional/ Rehabilitation | Hand rehabilitation, gait control, transfers and standing, FES-induced bicycling, arm cranking, FES systems for grasping and reaching, ejaculation, erectile dysfunction, dysphagia, cervical dystonia, diaphragm pacing, fecal incontinence, cough assistance, improvement of circulation, prevention and treatment of pressure sores, prevention or treatment of osteoporosis.<br>The termination (stimulating electrode) is positioned near the appropriate motor point. For example, for treatment of foot drop, the stimulating electrode may be located near the common peroneal nerve. The pick-up end is positioned on the leg, below the knee. The external stimulus generator delivers the required stimulation (for example, symmetric or asymmetric stimulation, 30 pulses per second, 200 µsec pulse width) upon triggering by a Foot Sensor, indicating heel on/heel off events. |
| Exercise (Spasticity/Pain Prevention) | Shoulder subluxation, cerebral palsy, Bell's palsy.<br>The termination (stimulating electrode) is positioned near the appropriate motor point. For example, for treatment of shoulder subluxation, the stimulating electrode may be positioned near the axillary nerve. The pick-up end is positioned below the skin in the shoulder area. The external stimulator is activated for a specific time, for example 1 hour, with symmetric or asymmetric stimulation, 30 pulses per second, 200 µsec pulse width, 5 sec ON and 5 sec OFF time. |
| Orthopedic Recovery | Prevention/reversal of muscle atrophy, knee replacement (post procedure pain)<br>Pain treatment can be delivered in several ways, namely by stimulating subcutaneously, stimulating peripheral nerves, or stimulating nerve roots, for example in the epidural space. Pain treatment stimulation usually requires higher frequencies (more pulses per second) as compared to the motor point stimulation—usually within the range of 30-50 pulses per second. The termination (stimulating end) is positioned in the appropriate area, and the pick-up end is positioned subcutaneously in a convenient space. An optimal location is one that does not cause the lead to cross the joints, or the pick-up end to be positioned in the moving area. The stimulation is initiated or stopped by the patient. |
| Systemic pain | Cancer pain, terminal illness pain, rheumatoid arthritis, osteoarthritis, phantom limb syndrome, bursitis, causalgia, multiple sclerosis, postherpetic neuralgia (shingles), synovitis, diabetic peripheral neuropathy, neuralgia.<br>For these purposes, the router system is applied in a similar manner as described for the orthopedic recovery applications. |
| Head and neck pain | Cluster headaches, dental disorders, migraine headaches, spondylosis, sprains, strains, suboccipital headaches, TMJ disorders, torticollis, whiplash, thoracic outlet syndrome.<br>For these purposes, the router system is applied in a similar manner as described for the orthopedic recovery applications. |
| Abdominal pain | Diverticulosis, dysmenorrhea, labor pain, Caesarean section (post-operative pain), incisions (post-operative pain).<br>For these purposes, the router system is applied in a similar manner as described for the orthopedic recovery applications. |
| Back pain | Facet syndrome, intercostal neuralgia, sacroiliac joint dysfunction, lumbago, lumbosacral pain, radiculitis, IVD syndrome, degenerative disc disease, spinal stenosis, sprains, strains, throacodynia, whole back pain.<br>For these purposes, the router system is applied in a similar manner as described for the orthopedic recovery applications. |
| Extremity pain | Sprains, strains, fractures, ischialgia, tendonitis, peripheral nerve injury, subdeltoid bursitis, frozen shoulder, impingement syndrome, epicondylitis, elbow pains, lateral epicondylitis, medical epicondylitis, radial tunnel syndrome, cubital tunnel syndrome, wrist pain, DeQuervain's tenosynovitis, Guyon's canal syndrome, hand pain, trigger finger and thumb, intersection syndrome, sciatica, knee pain, ankle pain, foot pain, stretch pain, thrombophlebitis, Raynaud's syndrome, Carpal Tunnel Syndrome.<br>For these purposes, the router system is applied in a similar manner as described for the orthopedic recovery applications. |
| Cosmetic | Electrical muscle stimulation to supplement regular training to fully exhaust muscle and to speed up recuperation to enhance maximum strength, maintain muscles at peak condition when normal exercise is suspended due to injury, tone up slack muscles, maintenance of peripheral circulation, relax muscles in case of strain, firm loose abdominal muscles to regain shape after childbirth.<br>For these purposes, the router system is applied in a similar manner as described for the functional/rehabilitation applications. |

The categories of conditions in Table 1 broadly relate to muscle stimulation (e.g., functional/rehabilitation stimulation, prevention of pain or spasticity, orthopedic recovery); pain treatment; and cosmetic applications. Functional/rehabilitation stimulation attempts to restore normal activity by activating selected muscles. Functional/rehabilitation stimulation can be continuous (e.g., as applied to urge incontinence) or repeatable (e.g., as applied to diaphragm-pacing, arm rehabilitation and gait control). Prevention of pain or spasticity includes stimulation applications for preventing pain, rather than suppressing pain. Orthopedic recovery includes muscle stimulation to prevent atrophy or prevention of post-procedure pain as associated with knee replacement. The same areas of the body may be stimulated; for example, radiculitis and lower back pain may overlap and have the same stimulation sites. Cosmetic applications include electrical stimulation targeted at cosmetic improvements, for example, electrical stimulation to help build and maintain muscles in peak condition (e.g., when normal exercise is suspended due to injury), maintain peripheral circulation, relax muscles following strain, or firm abdominal muscles following childbirth.

The present invention contemplates that the router system can be used to deliver electrical current to either external or implanted devices, to multiple target body tissues and to selective target body tissues as described below.

A. Delivery of Electrical Energy to External and Implanted Electrical Devices Using the Router System The present invention contemplates that the router system can be used to deliver electrical energy to one or more electrical devices which are powered by electrical current or which process electrical signals. Non-limiting examples of such electrical devices may include, for example, sensors (for example, ENG sensors, temperature sensors, pressure sensors, pH sensors, impedance sensors, and others known to one skilled in the art), amplifiers, filters, high voltage/constant current generators, switches, power supplies, batteries, battery-charging circuits, miniature rechargeable batteries, processors, frequency shifters, over-stimulation protection circuit, communication modules (wired or wireless) and other suitable devices known to those skilled in the art. Such electrical devices can be either external to the body or implanted within the body.

Implanted electrical devices are preferably biocompatible and non-toxic, or enclosed in a biocompatible case, generating no significant undesirable host response for the intended utility. For example, biocompatible sensors for assessing intra-body parameters and pre-processing circuits, communication circuits and power supply circuits are typically implanted within the body, such that raw data from implanted electrical devices, for example sensors, are transmitted to devices external to the body, for example, post-processing circuits which involve sophisticated algorithms, and greater processing power, space and power requirements compared to implanted devices.

i) Use of Router System with External Electrical Devices

The router system can be used to deliver electrical signals (monopolar and bi-polar signals) from target tissues within the body (electroneurographic or ENG signals) to external electrical devices. As an example, ENG is a common non-invasive test for examining the integrity of target tissues or organs by recording the spontaneous electrical activity of target tissues or organs, or by assessing the response of electrically excitable tissues or organs to stimulation. As a further example, the Auditory Brainstem Response (ABR) test provides objective information about the upper auditory system including the inner ear and brainstem. The target tissue is typically a nerve, for example a peripheral nerve, or organ for example a particular muscle innervated by a nerve.

Figure 2:
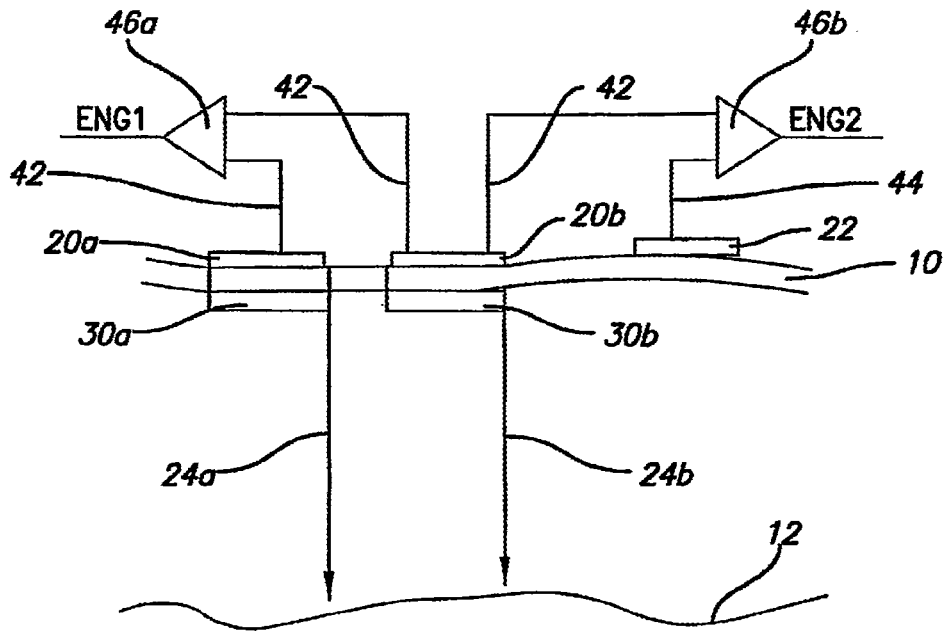
FIG. 2 is a schematic sectional view illustrating passive electrical conductors implanted subcutaneously for acquiring ENG signals.

FIG. 2 illustrates use of the router system for acquiring ENG signals. Two surface electrodes (for example, two surface cathodic electrodes 20a and 20b) are shown positioned separately over two implanted passive electrical conductors 24a and 24b. Electrical conductor 24a is focused in proximity to first point of the nerve 12, while electrical conductor 24b is in proximity to a second point of the same nerve 12. One surface reference electrode (for example, surface anodic electrode 22) is positioned on the skin 10.

Electrical conductors 24a and 24b deliver the electrical signal from the first and second points of the nerve 12, respectively. A differential amplifier 46 is provided to amplify the difference between the ENG signals at each of the first and second points of the nerve 12. Measurement of the amplified electrical signal is subsequently performed for example, by an RMS meter, peak meter, or oscilloscope, or digital data acquisition system. Differential amplifier 46a amplifies the signal at the first point (ENG1), while differential amplifier 46b amplifies the signal at the second point (ENG2). Alternatively, the ENG signal can be amplified by a differential amplifier connected between an electrical conductor 24 and a surface reference electrode (for example, surface anodic electrode 22).

The signal-to-noise ratio of the ENG signal can be improved by implanting an amplifier. The amplifier is implanted and connected between the conductors 24a and 24b. The amplifier amplifies the ENG signal and delivers the amplified signal via the electrical conductor 24 and termination 30 to an external signal acquisition device which is connected between the external surface electrodes 20a and 20b. The implanted amplifier and additional electronic circuits (for example, a series of amplifiers; a band pass filter to limit the bandwidth to only the signals of interest; or a band stop filter to prevent entry of 50 Hz or 60 Hz induced by the power lines) can be powered by an external generator delivering sub-threshold current through the skin 10.

Various conditions require use of the router system as described above to deliver electrical signals from target tissues within the body; for example, monitoring of gastric activity. Deviations in the electrical pattern of gastric activity can be indicative of different pathological conditions, for example, delayed gastric emptying time. The prior art approach is to record electrical activity by external electrodes, which have the disadvantage of being exposed to electrical noise and electrical signals from non-targeted organs. The present application contemplates that the router system as useful in the stomach area to improve the ability to monitor these signals.

ii) Use of Router System with Implanted Electrical Devices

The present invention contemplates that the router system can be also used to deliver electrical current to one or more implanted electrical devices 48. For this purpose, the implanted passive electrical conductor 24 has a pick-up end 26 and a delivery end 28 (rather than a stimulating end 28 per se). The pick-up end 26 allows a sufficient portion of electrical current to flow through the electrical conductor 24. The delivery end 28 delivers electrical current to one or more electrical devices 48.

Further, the present invention contemplates that the router system can be used for dual purposes, namely to deliver electrical current to one or more implanted devices 48, and to stimulate a target body tissue. For this purpose, the implanted passive electrical conductor 24 has one end which is a pick-up end 26 and another end which acts as both a delivery end 28 to deliver electrical current to one or more implanted electrical devices 48, and a stimulating end 28 to deliver electrical current to a target body tissue.

For illustrative purposes, the electrical conductor 24 is schematically shown in FIGS. 3, 4, 5 and 6 as being positioned under the surface cathodic electrode 20; however, it will be appreciated by those skilled in the art that the electrical conductor 24 can be positioned below either or both of the surface cathodic electrode 20 or the surface anodic electrode 22.

Figure 3:
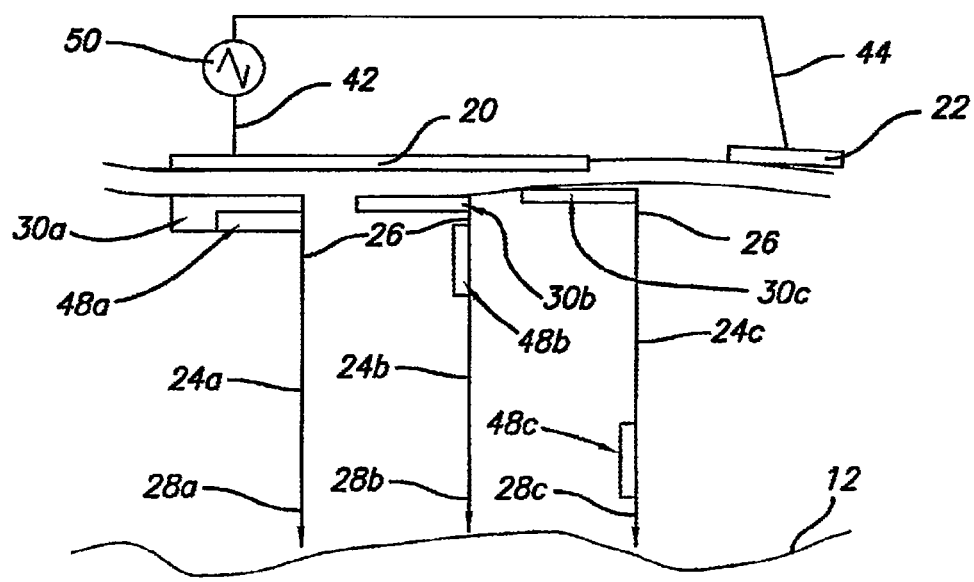
FIG. 3 is a schematic sectional view illustrating passive electrical conductors implanted subcutaneously and incorporation of implanted electrical devices with the conductors.

Implanted electrical devices 48 can be positioned anywhere along the electrical conductor 24 or can be formed as part of the termination 30 for example, of the pick-up end 26. FIG. 3 illustrates several approaches as examples for incorporating implanted electrical devices 48 with the router system. An external stimulator 50 delivers sub-threshold (or above threshold) transcutaneous electrical current picked up by a termination 30a, 30b, 30c. Implanted devices 48 can be built as part of the termination 30a (for example, device 48a); as separate but adjacent to the termination 30b (for example, device 48b); or as separate and remote relative to the termination 30c (e.g., implanted near the nerve as for example, device 48c).

Figure 4:
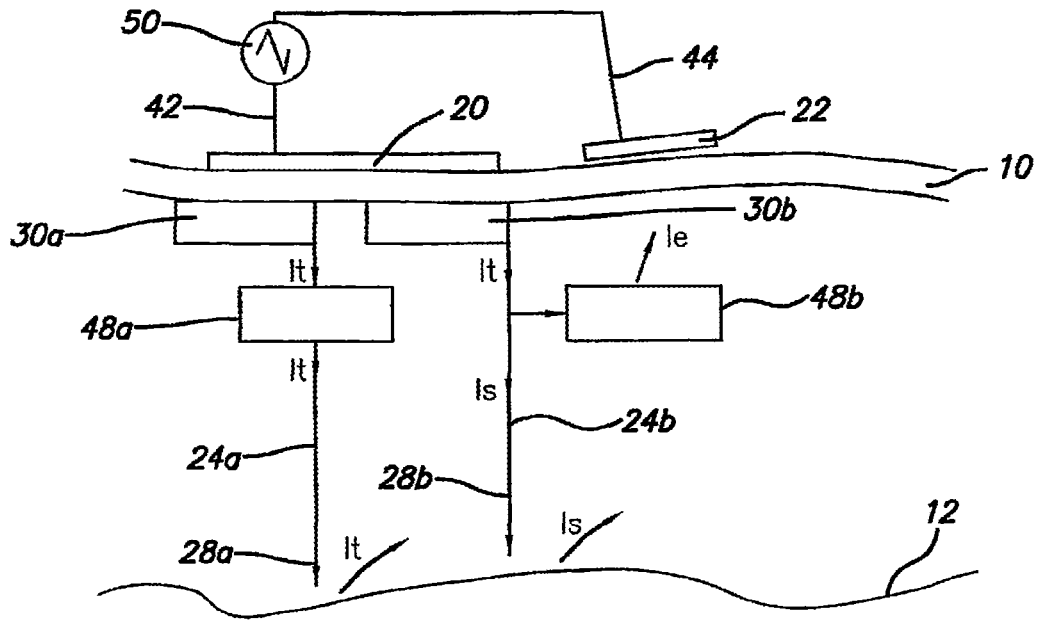
FIG. 4 is a schematic sectional view illustrating passive electrical conductors implanted subcutaneously and connection of implanted electrical devices in series or in parallel with the conductors.

As shown in FIG. 4, the implanted electrical device 48 can be connected in series, as illustrated by the positioning of device 48a. The external stimulator 50 provides electrical current to the surface cathodic electrode 20 which is delivered to termination 30a. The electrical current picked up by termination 30a (designated as "It") then flows through device 48a, continues through the electrical conductor 24a and the stimulating end 28a to be delivered into the target body tissue, for example nerve 12. The electrical current returns through the body tissue and the surface anodic electrode 22 to the external stimulator 50. Alternatively, a "parallel" connection, as illustrated by the positioning of device 48b, can be used. The device 48b consumes a portion (designated as "Ie") of the "It" electrical current picked up by the termination 30b. The return current is shown flowing from device 48b through body tissue to the surface anodic electrode 22. The electrical current (designated as "Is" which is It-Ie) flows via the electrical conductor 24b to the stimulating end 28b and returns to the surface anodic electrode 22 through body tissue.

Various conditions require use of the router system as described above to deliver electrical signals to implanted devices within the body. For example, implanted amplifiers can improve the quality of the acquisition of the intra-body electrical signals. Electrical current is delivered to power the amplifier. The required current can be, for example, less than 1 mA, and at a frequency of higher than 50 KHz in order to pass easily through the skin, to avoid sensation or stimulation, or to avoid interference with the measured ENG signal.

Figure 5:
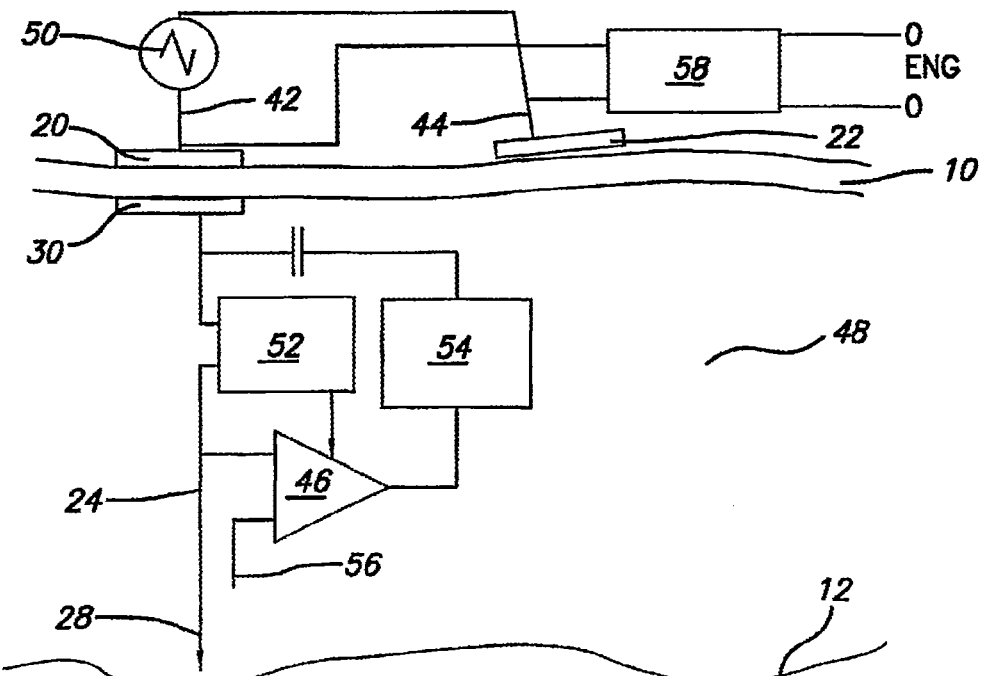
FIG. 5 is a schematic sectional view illustrating a passive electrical conductor implanted subcutaneously and incorporation of an ENG sensing device with the conductor.

As an example, FIG. 5 illustrates the use of the router system to deliver electrical energy to implanted devices for acquiring ENG signals from a target tissue, for example a nerve 12. The implanted devices shown generally at 48 include a power supply 52, a differential amplifier 46, a frequency shifter 54 and a reference electrode 56. The reference electrode 56 serves to measure the difference of potentials between it and the nerve 12, as picked by the stimulating end 28 and a reference electrode located elsewhere in the tissue. The reference electrode 56 can be positioned within the distance of several millimeters to several centimeters of the stimulating end 28. The external stimulator 50 delivers a sub-threshold signal, which can be, for example, a sinusoidal signal having a frequency outside those of the ENG, to the surface cathodic electrode 20 which delivers the electrical current to termination 30. The electrical current, picked up by termination 30, is then rectified and stabilized by the power supply 52. In order to deliver energy through the tissue without causing skin irritation, pain, or local muscle contractions, the external stimulator 50 is used to deliver a symmetrical waveform of high frequency, for example, usually higher than 30-50 KHz. In order to power the electronic circuitry, and specifically the differential amplifier 46, DC current is required. Power supply 52 rectifies the current delivered by the stimulator 50 to pick-up electrode 30, and than stabilizes it and creates the required voltages/currents. The power supply 52 in turn delivers power to the differential amplifier 46. The differential amplifier 46 amplifies the nerve signal 12 picked up by the stimulating end 28. The amplified signal is then fed back to the termination 30 to the external cathodic electrode.

Specifically, the current flows from the external stimulator 50 to the surface cathodic electrode 20, via capacitive coupling to termination 30, via power supply 52 to electronic circuits, e.g. amplifier 46, continues to the electrical conductor 24, stimulating end 28, and returns through the tissue to the surface anodic electrode 22, to the external stimulator 50. It will be appreciated by those skilled in the art that the signals generated by the amplifier 46 and the frequency shifter 54 can be superimposed on the same current path. These signals do not interfere with the measurements, since a frequency shifter 54 can be optionally provided to shift the amplified ENG signal outside the frequency spectrum of the original ENG signal, thereby preventing interference with the original ENG signal. Several techniques are known in the art to achieve frequency shifting, for example, amplitude modulation (where the signal is mixed with a carrier wave, resulting in shifting the original signal spectrum to be around the carrier frequency), single side band modulation (SSB), frequency modulation (FM) and phase modulation (PM). The signal can be transmitted in its analog form or using digital encoding. The amplified signal can be processed by using analog or digital processing techniques; for example, the amplified signal can be filtered by an external filter 58, shifted back to the original frequency, and output for the further processing.

As is known to those skilled in the art, time division could be used. In one time slot, the ENG signal is amplified and recorded in the implanted module or recording device, and in the next time slot, the recorded signal is transmitted through the termination 30. Wireless transmission of the information also can be applicable.

Figure 6:
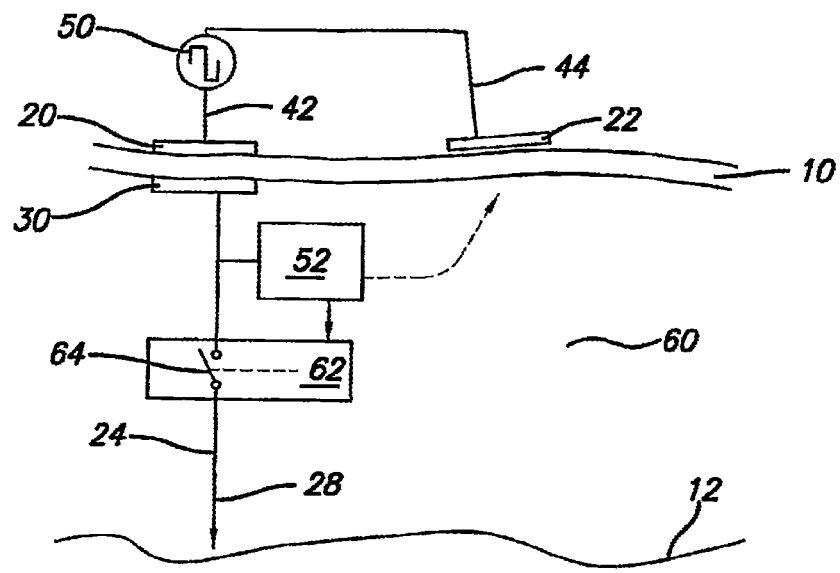
FIG. 6 is a schematic sectional view illustrating a passive electrical conductor implanted subcutaneously and incorporation of an over-stimulation protection circuit with the conductor.

As a further example, FIG. 6 illustrates use of the router system to deliver electrical energy to an over-stimulation protection circuit shown generally at 60. A controller 62 and a power supply 52 are implanted in connection with the passive electrical conductor 24. The controller 62 includes a switch 64 for selectively disconnecting the stimulating end 28. The disconnection can be performed, for example, if the electrical current exceeds a pre-defined threshold. Alternatively, an external device can be used to provide a signal to connect or disconnect the stimulating end 28. The power supply 52 can incorporate a non-volatile memory to store a serial number or code number of an external stimulator 50. The external stimulator 50 transmits a number and, if the number matches the stored number, the stimulating end 28 is then connected; otherwise, the stimulating end 28 is disconnected. This approach prevents use of unauthorized or unapproved external stimulators.

As yet a further example, the router system can be used to deliver electrical energy to charge implanted batteries. For example, miniature implantable stimulators can be charged using this approach.

Figure 7:
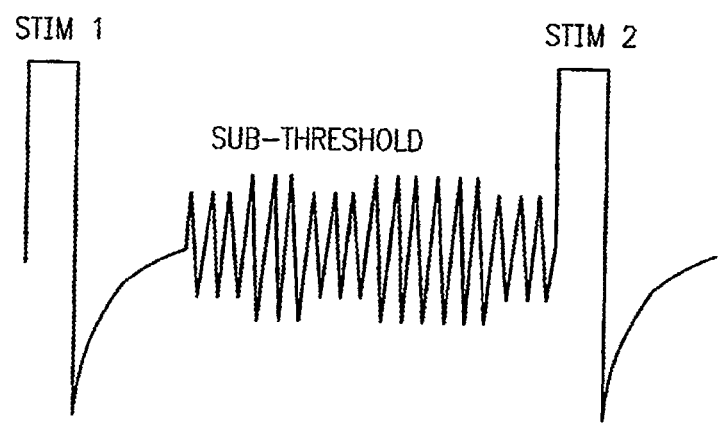
FIG. 7 is a schematic view illustrating waveforms for transmitting stimulus and data.

One of the possibilities for transmitting both stimulus and data is shown in FIG. 7. One possible approach is to transmit the data between the successive stimuli. The data is transmitted, for example, by modulating a sub-threshold sine wave. Amplitude modulation is shown in the example; however, various other modulation techniques alternatively could be used.

B. Stimulation of Multiple Target Body Tissues Using the Router System

International Publication No. WO 2005/070494 A1 and U.S. patent application Ser. No. 11/337,824 describe an embodiment of the router system as involving a plurality of implants for electrically stimulating more than one target body tissue independently or in unison to activate neural impulses. The presence of multiple implants necessitates positioning of a plurality of surface cathodic electrodes, and one or more surface anodic electrodes appropriately relative to the implants to stimulate the different target body tissues independently or in unison. One or more external stimulators are required. The present invention contemplates several arrangements as set out below.

Figure 8A:
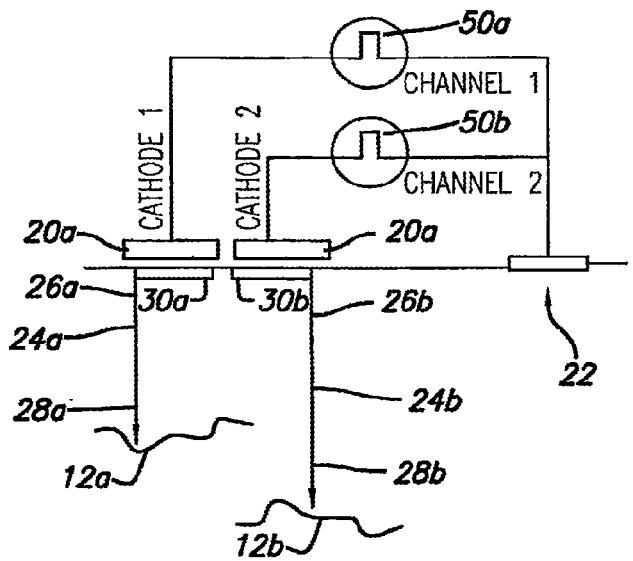
FIG. 8A is a schematic view illustrating two channels, using two surface cathodic electrodes, two terminations and a common surface anodic electrode.
Figure 9A:
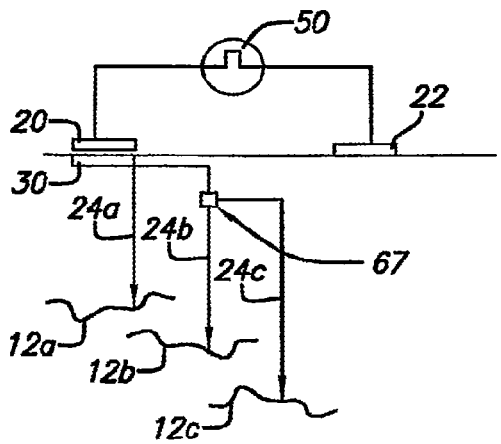
FIG. 9A is a schematic view illustrating several electrical conductors connected to the same termination.
Figure 9B:
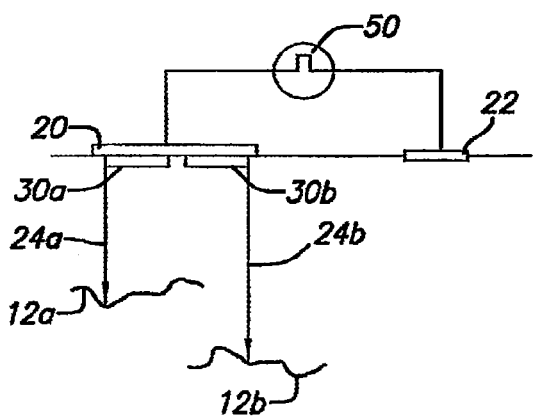
FIG. 9B is a schematic view illustrating several electrical conductors connected to terminations which are positioned under a common surface cathodic electrode.

For illustrative purposes, the electrical conductor 24 is schematically shown in FIGS. 8A, 9A and 9B as being positioned under the surface cathodic electrode 20; however, it will be appreciated by those skilled in the art that the electrical conductor 24 can be positioned below either or both of the surface cathodic electrode 20 or the surface anodic electrode 22.

a) A Plurality of Surface Cathodic Electrodes 20 Sharing One Surface Anodic Electrode 22, and One or More External Stimulators 50 can be Used.

Figure 8B:
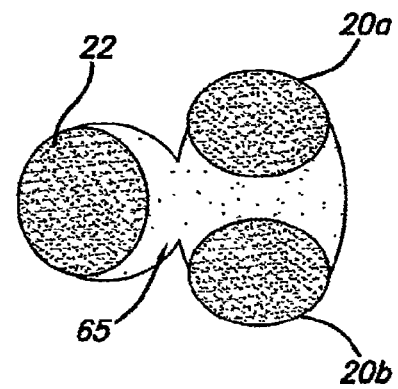
FIG. 8B is a schematic view illustrating a single patch, two-channels surface electrode.

In this arrangement, each surface cathodic electrode 20a, 20b is positioned over a separate implanted passive electrical conductor 24a, 24b which extends to a different target body tissue 12a, 12b. Each electrical conductor 24a, 24b forms an electrical termination 30a, 30b at its pick-up end 26a, 26b, and provides a conductive pathway for at least a portion of the electrical current flowing between the plurality of surface cathodic electrodes 20a, 20b and the one anodic electrode 22. Each surface cathodic electrode 20a, 20b can be connected either to separate stimulators 50a, 50b (Le., creating two separate channels as shown in FIG. 8A) or to a single multi-channel stimulator 50 (for example, a single patch, two-channels surface electrode arranged on conductive material 65 as shown in FIG. 8B). The surface anodic electrode 22 can be connected to each of the separate stimulators 50a, 50b or to the single multi-channel stimulator 50.

b) One Surface Cathodic Electrode 20 and One Surface Anodic Electrode 22 Sharing One External Stimulator 50 can be Used.

In this arrangement, the surface cathodic electrode 20 is positioned over one termination 30 to which more than one separate implanted passive electrical conductors 24a, 24b, 24c are connected by any suitable means, for example, a crimp connection 67 or by welding (FIG. 9A). In an alternate arrangement, the surface cathodic electrode 20 can be positioned over more than one separate termination 30a, 30b in order to provide electrical current to more than one electrical conductor 24a, 24b (FIG. 9B).

c) A Segmented Surface Cathodic Electrode

In order to compensate for a possible misalignment of the surface cathodic electrode 20 and the stimulation, the surface cathodic electrode 20 can be divided into segments, with each segment being connected individually to an external stimulator 50 by a switching matrix. The switches are operated either manually or by a controller. Electrical stimulation is thereby delivered mainly to the area of the surface cathodic electrode 20 which is positioned above the termination 30 of the electrical conductor 24. It will be appreciated by one skilled in the art that appropriate algorithms can be determined to deliver optimal stimulation; for example, by choosing the segment having the lowest impedance. This arrangement provides easier alignment with the electrical conductor 24; a smaller skin surface 10 conducting the electrical current; and a way of balancing stimulation when a plurality of electrical conductors 24 are present.

The situation might arise where the stimulation site, for example the back, might not be easily accessible. A solution is to implant the termination 30 in an accessible place, and to tunnel a lead to the target body tissue. The stimulation site can be either focused (i.e., adjacent the target body tissue) or dispersed (i.e., not adjacent to any specific target body tissue).

The above arrangements require one or more external stimulators 50 for supplying electrical current to the surface cathodic and anodic electrodes 20, 22.

Suitable external stimulators 50 include an external stimulator 50 connected to electrodes 20, 22, a portable stimulator 50 attached to electrodes 20, 22 and including a power source, or a portable stimulator 50 controlled by a remote control.

The external stimulator 50 can be simply connected by the cathodic and anodic wires 42, 44 to the surface cathodic and anodic electrodes 20, 22 placed on the skin 10 (as shown in FIG. 1). However, attachment of the electrodes 20, 22 might be challenging, requiring individual placement of the electrode 20, 22 and individual connection of the electrode 20, 22 to the stimulator 50. The inconvenience may be extreme on unreachable body parts, e.g., on the shoulder. Further, the size of the stimulator 50 might limit mobility of the subject. While acceptable for applications requiring limited duration of stimulation, it might be limiting for other applications.

Alternatively, a portable stimulator 50 which includes cathodic and anodic electrodes 20, 22 and display and control buttons can be used. However, access to the stimulator's control and display buttons might be inconvenient and/or limited. For example, placement on the shoulder will prevent access to such display and control buttons. The portable stimulator 50 includes, but is not limited to, multiple-use electrodes, a limited user interface (on/off LED) and remote control unit with display and control functions. However, this set-up requires an additional device in the form of the remote control, and additional regulatory aspects (for example, FCC, European Radio regulations). A single remote unit can be used to control several stimulators 50 which might require more complicated communication protocol and unique ID for each stimulator 50 in order to prevent collision between different users.

The difficulty of positioning surface cathodic and anodic electrodes 20, 22, for example on the shoulder, can be overcome by using a flexible garment or a rigid orthosis. Non-limiting examples include the T-CUFF™ (A. Prochazka, University of Alberta) comprising a glove in which the stimulator is embedded, and the NESS H200™ (NESS Ltd., Israel) comprising a rigid orthosis having embedded electrodes and a stimulator connected by a wire.

Various conditions require use of the router system as described above to deliver electrical signals to multiple target body tissues; for example, arm rehabilitation generally requires alternative operation of flexors and extensors. The pick-up electrodes 20 for activating flexors and extensors can be positioned under the skin 10 in the forearm. The activation may be achieved, for example, by applying pulses of 200 μsec duration, 30 pulses per second, for several seconds, alternating between flexors and extensors.

C. Use of the Router System to Stimulate Body Tissues Selectively

Although the router system can be used to stimulate multiple target body tissues as discussed above, greater stimulation of particular body tissues over others may be needed. For example, in subcutaneous stimulation for pain treatment, it may be required to stimulate the entire area of pain. The present invention further contemplates that the router system can be used to deliver electrical current selectively.

Figure 10A:
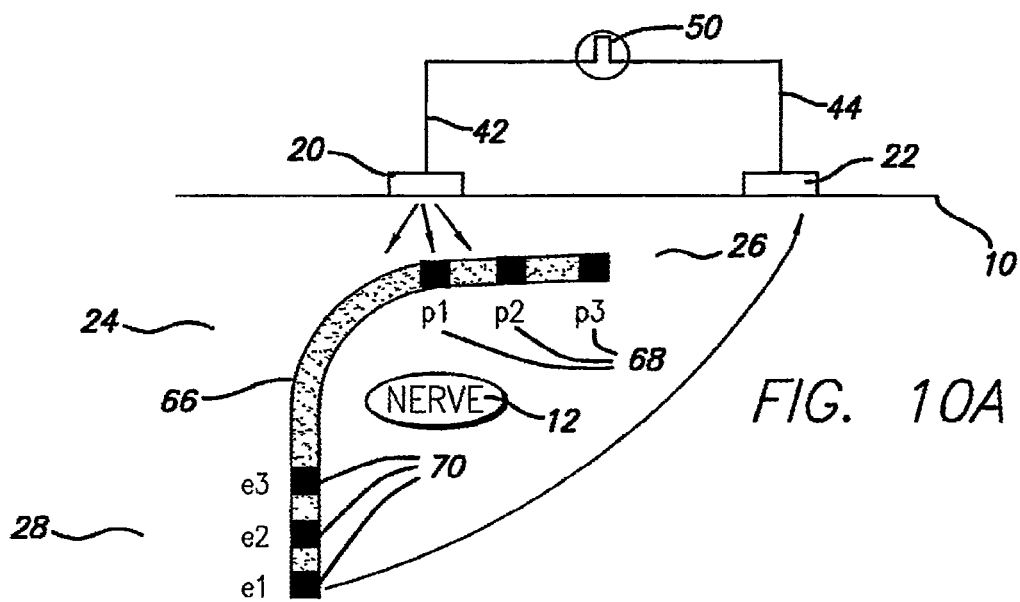
FIG. 10 is a schematic sectional view illustrating a passive electrical conductor implanted subcutaneously, with the conductor having a lead incorporating three conductive stimulating electrodes designated as e1, e2 and e3 and connected to three conductive pick-up electrodes p1, p2 and p3, respectively
Figure 10B:
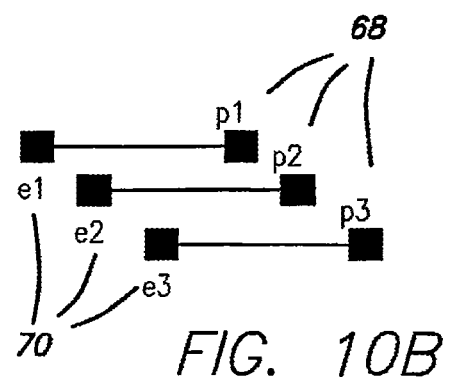

The passive electrical conductor 24 can be formed from a lead 66 having a pick-up end 26 and a stimulating end 28 (for example, as shown in FIG. 10). The pick-up end 26 can comprise one or more conductive pick-up electrodes 68, and the stimulating end 28 can comprise one or more conductive stimulating electrodes 70. The conductive stimulating electrode 70 on the lead 66 usually has a optimal size. If the conductive stimulating electrode 70 is too small, for example, having surface of less than 10 mm$^2$, the transfer impedance between the conductive stimulating electrode 70 and the target body tissue 12 will be too high. If the conductive stimulating electrode 70 is too large, for example, greater than 50-60 mm$^2$, the current density delivered by the conductive stimulating electrode 70 will be too low to activate target body tissue, for example the nerve 12. The optimal length of the conductive stimulating electrode 70 is usually of several millimeters, preferably 3-4 mm, having an area of about 20 mm$^2$. It is generally positioned in the vicinity of the targeted nerve, preferably 1-3 mm, more preferably 1 mm or less. Due to constraints of implantation and concern of mechanical nerve damage, the conductive stimulating electrode 70 is generally not placed touching the nerve; otherwise, the required stimulation levels will be too high, causing undesirable sensations and/or local muscle contractions.

Since such accuracy in insertion of the lead 66 is challenging, a solution is to implant an array of electrodes 68, 70 and to activate the electrodes 68, 70 in the desired locations, or to implant a combination of electrodes 68, 70 resulting in an optimal delivery of stimulation, known as "current steering." The ability to select different pick up or stimulating electrodes 68, 70 during or after implantation of the lead 66 can be beneficial; for example, if the stimulating end 28 or the target tissue have migrated within the body and the selected stimulating electrode 70 is no longer in the vicinity of the target body tissue; or if any wires between the pick-up electrode 68 and the stimulating electrode 70 become damaged.

Figure 11:
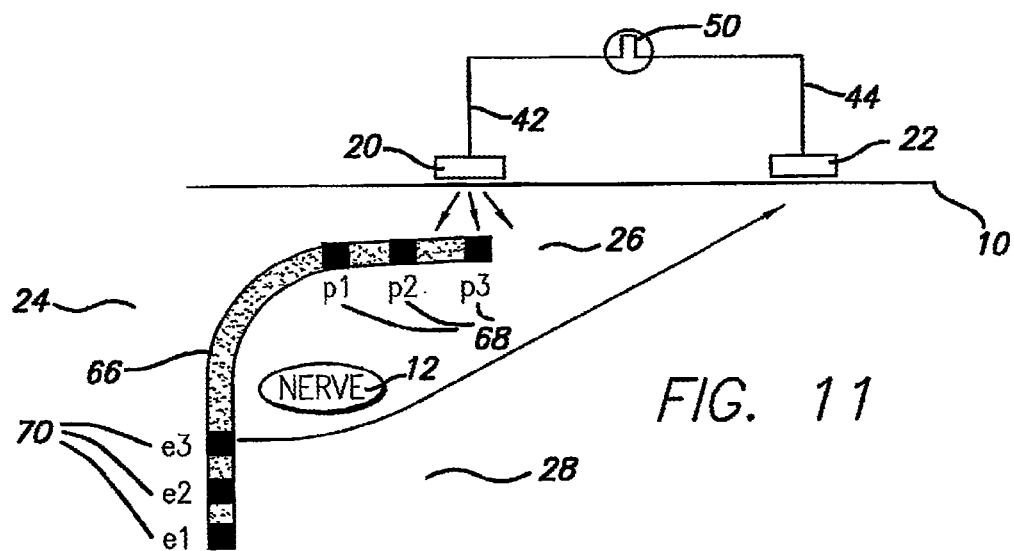
FIG. 11 is a schematic sectional view illustrating a passive electrical conductor implanted subcutaneously, and positioning of the surface cathodic electrode over the conductive pick-up electrode p3 to divert electrical current via the p3-e3 path.

FIG. 10 (panel A) shows an implanted passive electrical conductor 24 comprising a lead 66 incorporating three conductive stimulating electrodes 70 designated as e1, e2 and e3 and three conductive pick-up electrodes 68 designated as p1, p2 and p3, respectively. FIG. 10 (panel B) shows that each conductive pick-up electrode 68 has a corresponding conductive stimulating electrode 70. Alternatively, each conductive pick-up electrode 68 can have more than one corresponding conductive stimulating electrode 70. Conductive stimulating electrode e3 is positioned closest to the target body tissue (i.e., nerve 12). A surface cathodic electrode 20 is positioned on the skin 10 above the conductive pick-up electrode "p1." The electrical current provided to the surface cathodic electrode 20 flows through "p1" and "e1" to the surface anodic electrode 22 (e1 is the corresponding conductive stimulating electrode for conductive pick-up electrode p1). Most of the electrical current is thus not delivered to the nerve 12. However, as shown in FIG. 11, positioning the surface cathodic electrode 20 over the conductive pick-up electrode p3 diverts the current via the p3-e3 path, resulting in the electrical current passing in the vicinity of the nerve 12 to provide stimulation (e3 is the corresponding conductive stimulating electrode for conductive pick-up electrode p3).

To simplify the positioning of the surface cathodic electrode 20 over the conductive pick-up electrodes 68, the surface cathodic electrode 20 can be sized to overlap one or more conductive pick-up electrodes 68, although delivery of the electrical current might be less focused. Further, one or more conductive pick-up electrodes 68 can be exposed, while the remaining conductive pick-up electrodes 68 are insulated with a layer of single use or removable and re-attachable electrical insulation. The insulation layer can be scratched, cut or dissolved during the fitting process (i.e., testing which conductive pick-up and stimulating electrodes 68, 70 are the most efficient to deliver stimulation to the target body tissue). Alternatively, the insulation layer can be removed and re-attached to the conductive pick-up electrode 68 by suitable means, for example a sleeve which is either slidable over the conductive pick-up electrode 68 to provide insulation preventing the flow of electrical current, or removable and re-attachable to expose the conductive pick-up electrode 68, thereby receiving the flow of electrical current.

Figure 12A:
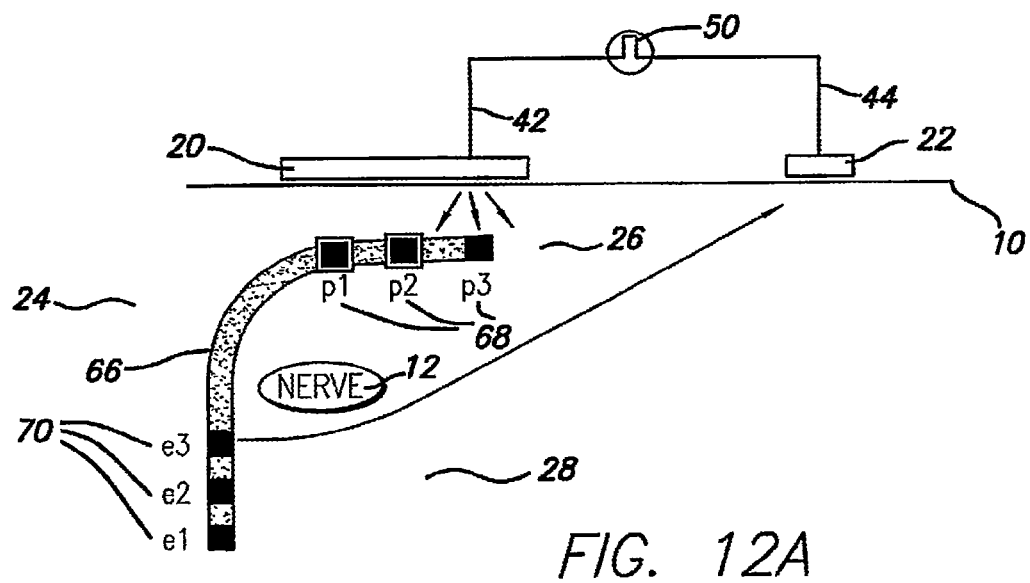
FIG. 12A is a schematic sectional view illustrating a passive electrical conductor implanted subcutaneously, and insulation of conductive pick-up electrodes p1 and p2 and exposure of conductive pick-up electrode p3 to divert electrical current to stimulating electrode e3.
Figure 12B:
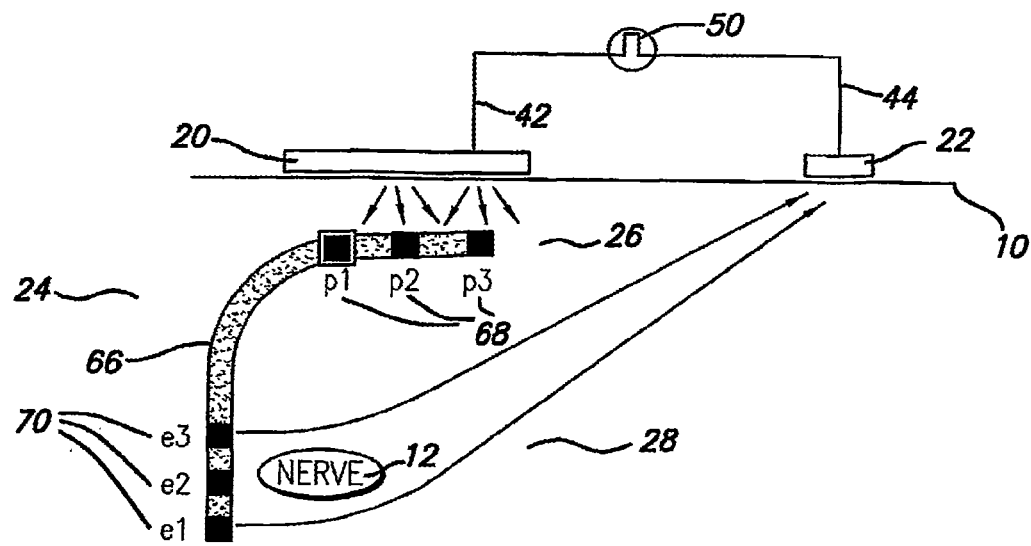
FIG. 12B is a schematic sectional view illustrating a passive electrical conductor implanted subcutaneously, and insulation of conductive pick-up electrode p1 and exposure of conductive pick-up electrodes p2 and p3 to divert electrical current to stimulating electrodes e2 and e3.

FIG. 12A illustrates conductive pick-up electrodes p1 and p2 which are insulated and conductive pick-up electrode p3 which is exposed. The electrical current is subsequently diverted to the conductive stimulating electrode e3 positioned in the vicinity of the nerve 12 (e3 is the corresponding conductive stimulating electrode for conductive pick-up electrode p3). FIG. 12B illustrates the nerve 12 positioned between conductive stimulating electrodes e2 and e3. Insulation of conductive pick-up electrode p1 and exposure of conductive pick-up electrodes p2 and p3 diverts electrical current to conductive stimulating electrodes e2 and e3, thereby stimulating the nerve 12.

Figure 12C:
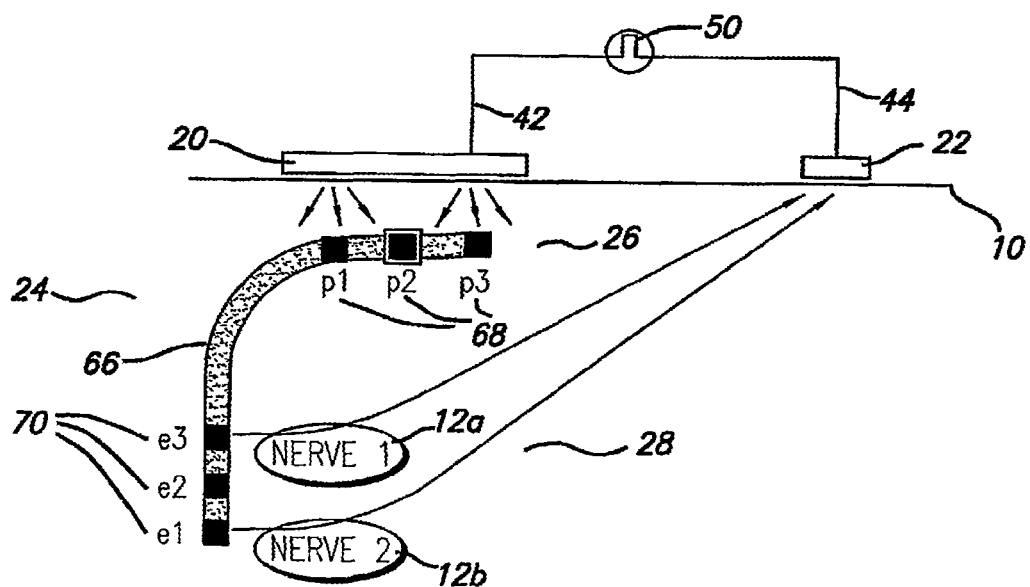
FIG. 12C is a schematic sectional view illustrating a passive electrical conductor implanted subcutaneously, and insulation of conductive pick-up electrodes p2 and exposure of conductive pick-up electrodes p1 and p3 to divert electrical current to conductive pick-up electrodes e1 and e3.

In a further aspect, FIG. 12C illustrates two nerves 12a, 12b, with conductive stimulating electrode e3 positioned at one nerve 12a and conductive stimulating electrode e1 positioned at the other nerve 12b. Conductive pick-up end p2 is insulated, while conductive pick-up electrodes p1 and p3 are exposed. Electrical current is diverted to conductive pick-up electrodes p1 and p3, which deliver the electrical current to conductive pick-up electrodes e1 and e3 respectively, to stimulate the nerves 12a, 12b.

Figure 12D:
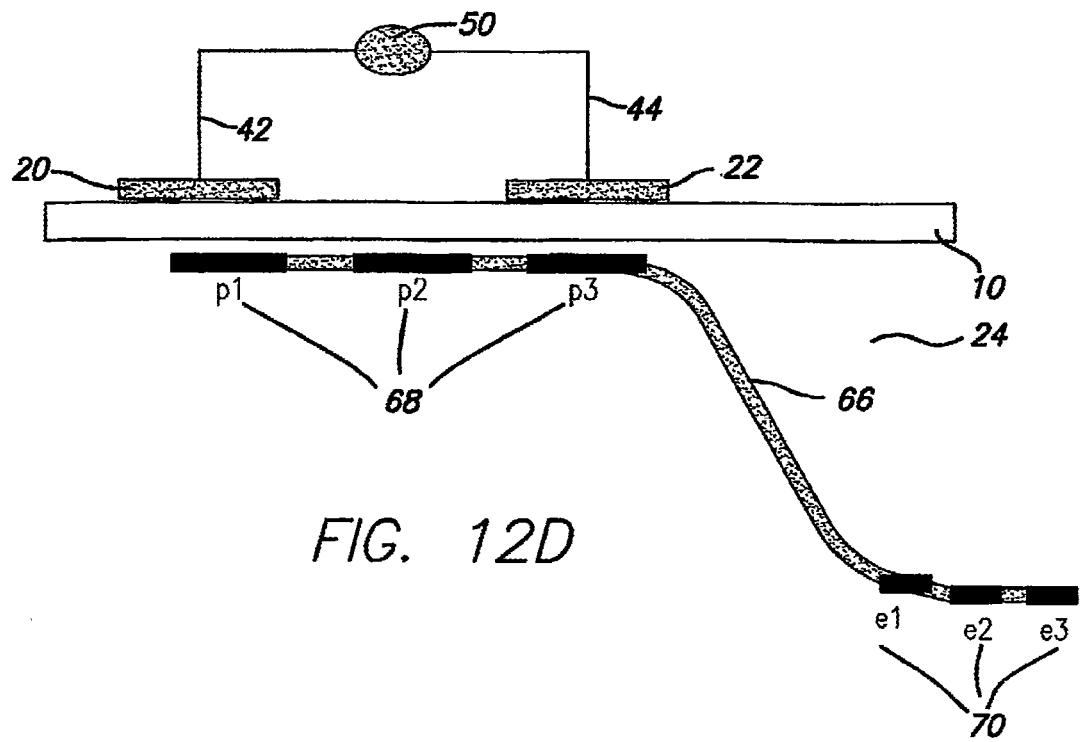
FIG. 12D is a schematic sectional view illustrating a passive electrical conductor implanted subcutaneously, and positioned below both of the surface cathodic and anodic electrodes.

For illustrative purposes, the electrical conductor 24 is schematically shown in FIGS. 10, 11, 12A, 12B and 12C as being positioned under the surface cathodic electrode 20; however, it will be appreciated by those skilled in the art that the electrical conductor 24 can be positioned below either or both of the surface cathodic electrode 20 or the surface anodic electrode 22. For example, FIG. 12D illustrates an implanted passive electrical conductor 24 having a lead 66 incorporating three conductive pick-up electrodes 68 designated as p1, p2 and p3 and three conductive stimulating electrodes 70 designated as e1, e2 and e3, respectively. The conductive pick-up electrodes 68 of the lead 66 are positioned below both the surface cathodic and anodic electrodes 20, 22 Conductive pick-up electrode p1 is positioned below the surface cathodic electrode 20, and conductive pick-up electrode p3 is positioned below the surface anodic electrode 22 (e1 is the corresponding conductive stimulating electrode for conductive pick-up electrode p1, while e3 is the corresponding conductive stimulating electrode for conductive pick-up electrode p3).

Figure 12E:
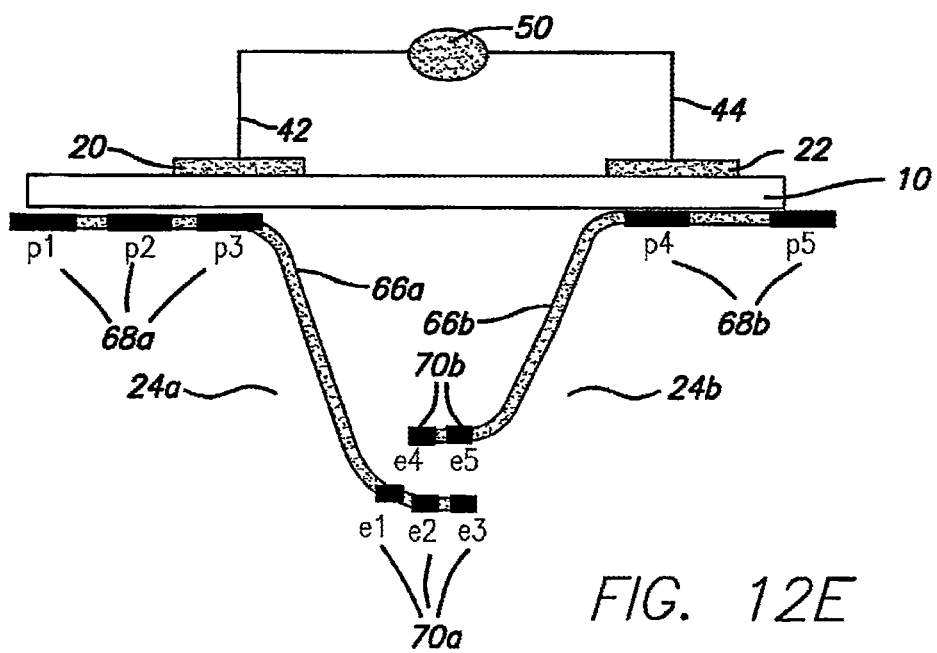
FIG. 12E is a schematic sectional view illustrating two passive electrical conductors implanted subcutaneously, with one conductor being positioned below the surface cathodic electrode, and the other conductor being positioned below the surface anodic electrode.

FIG. 12E illustrates two implanted passive electrical conductors 24a, 24b. Electrical conductor 24a has a lead 66a incorporating three conductive pick-up electrodes 68a designated as p1, p2 and p3, and three conductive stimulating electrodes 70a designated as e1, e2 and e3, respectively. Electrical conductor 24a is positioned below the surface cathodic electrode 20, with conductive pick-up electrode p3 located below surface cathodic electrode 20 (e3 is the corresponding conductive stimulating electrode for conductive pick-up electrode p3). Electrical conductor 24b has a lead 66b incorporating two conductive pick-up electrodes 68b designated as p4 and p5, and two conductive stimulating electrodes 70b designated as e4 and e5, respectively. Electrical conductor 24b is positioned below the surface anodic electrode 22, with conductive pick-up electrode p4 located below the surface anodic electrode 22 (e4 is the corresponding conductive stimulating electrode for conductive pick-up electrode p4).

Figure 13:
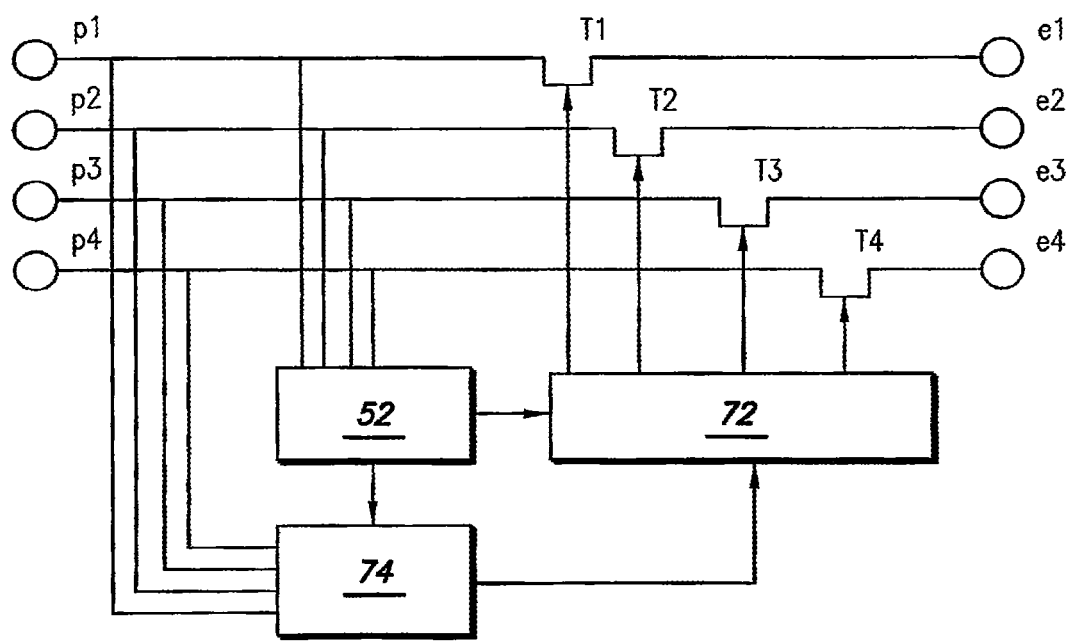
FIG. 13 is a schematic view illustrating wireless selection of conductive pick-up/stimulating electrodes by electronic circuits based on non-volatile memory.

In yet a further aspect, wireless or wired selection of conductive pick-up and stimulating electrodes 68, 70 can be achieved by including, for example, electronic circuits based on non-volatile memory 72 (FIG. 13). The electrical current is picked by the conductive pick-up electrodes (p1, p2, p3, p4) and passes through an implanted power supply 52 to operate the non-volatile memory 72. Outputs of the non-volatile memory 72 drive switches (T1, T2, T3, T4) which enable or disable the path of electrical current between the conductive pick-up electrodes (p1, p2, p3, p4) and the conductive stimulating electrodes (e1, e2, e3, e4). A pre-defined pattern picked by the conductive pick-up electrodes 68 activates a programming circuit 74 to change the non-volatile memory 72 so that different patterns of the conductive stimulating electrodes 70 can be selected.

Alternatively, a switching matrix based on shape memory alloy (SMA) can be used. SMA is a metal which remembers its geometry. After a sample of SMA has been deformed from its original conformation, it regains its original geometry by itself during heating when exposed to a temperature above a particular threshold. By heating the SMA contact, it changes its shape and disconnects the stimulating electrode. For example, SMA changes its shape when heated to 5° C. above the body temperature, and it will maintain this new shape unless it will be cooled 5° C. below the body temperature.

Transcutaneous heating performed for example, by an ultrasonic beam, can operate the SMA based switch from ON to OFF. Non-limiting examples of SMA include copper-zinc-aluminum, copper-aluminum-nickel, and nickel-titanium alloys.

Testing of conductive pick-up and stimulating electrodes 68, 70 can be conducted, for example during implantation. Following implantation of the conductive stimulating electrodes 70 at the target body tissue, the conductive pick-up electrodes 68 still protrude percutaneously. The conductive pick-up electrodes 68 can be connected directly to the external stimulator 50, and the best conductive pick-up electrode 68 may be chosen. The external stimulator 50 is connected (e.g. with a clamp) to a certain conductive pick-up electrode or a combination of electrodes. The response is observed. For example, in the case of motor point stimulation, the combination which causes the lowest activation threshold may be selected. As a further example, in the case of pain treatment, the patient response is examined. If the stimulation causes a tingling sensation and the pain disappears, it is an indication of successful combination of the electrodes.

Figure 14A:
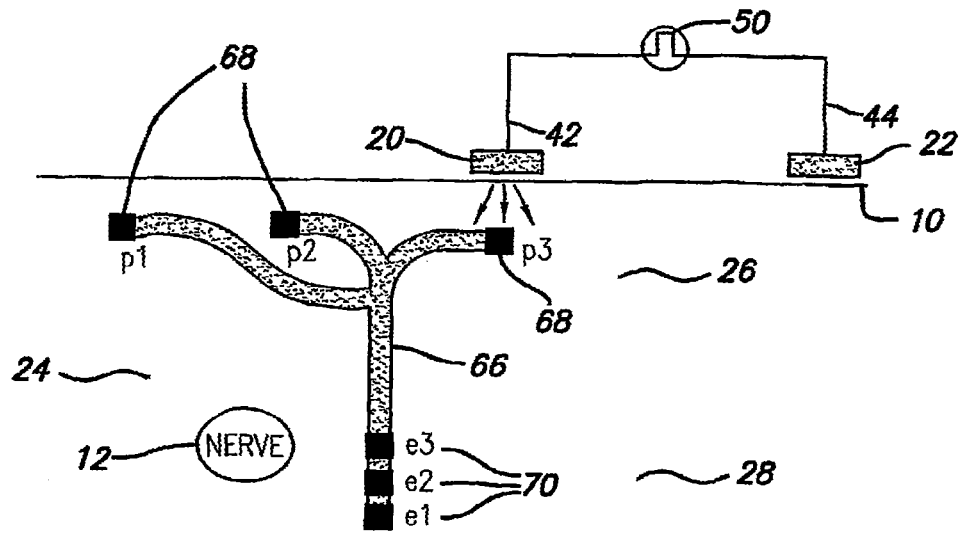
FIG. 14A is a schematic sectional view illustrating a passive electrical conductor implanted subcutaneously, and a branched arrangement of the conductive pick-up electrodes.
Figure 14B:
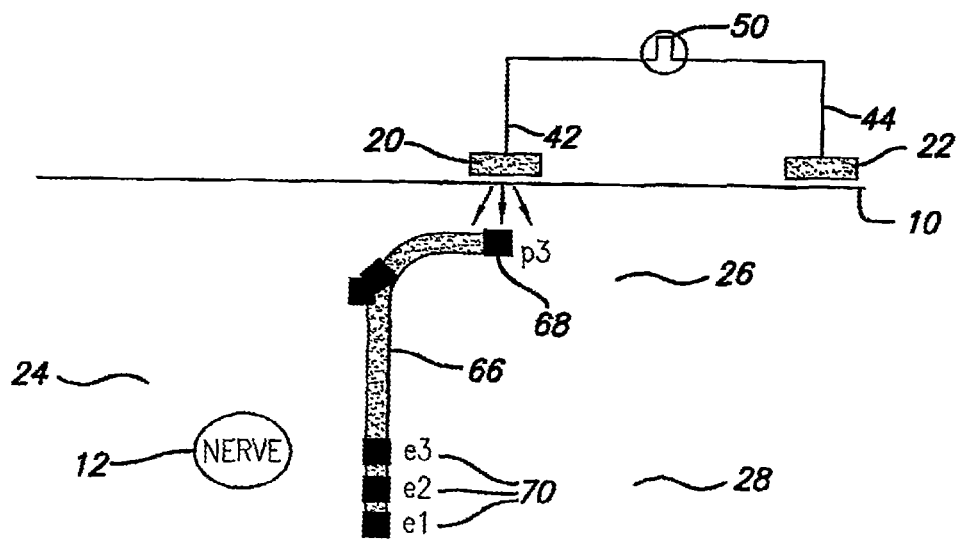
FIG. 14B is a schematic sectional view illustrating the conductive pick-up electrodes of FIG. 14A following trimming.

One method of selecting pick-up electrodes 68 is to position the surface electrode (for example, surface cathodic electrode 20) over a particular implanted pick-up electrode (for example, pick-up electrode p3 as shown in FIG. 14A). Alternatively, electrodes which are not used may be trimmed during the implantation and fitting procedure (FIG. 14B).

Non-limiting examples of leads 66 useful for the described "current steering" and other applications described herein are illustrated in FIGS. 15A-15E. FIG. 15A shows a lead 66 having a conductive pick-up electrode 68 and three conductive stimulating electrodes 70. Insulating backing 76 can be attached to the conductive pick up electrode 68 to increase efficacy of the pick-up end 26. Suitable insulating backing 76 can include, for example, silicone, polyester fiber such as Dacron™ (Invista, Inc) or other appropriate biocompatible materials. FIG. 15B illustrates a lead 66 having a conductive pick-up coil electrode 68 with insulating backing 76. FIG. 15C shows a lead 66 having a conductive pick-up circular electrode 68 and three conductive stimulating electrodes 70, with FIG. 15D showing a conductive pick-up circular electrode 68 with insulating backing 76 and three conductive stimulating electrodes 70. FIG. 15E shows a lead 66 having a conductive pick-up electrode 68 to which also insulating backing 76 can be attached, for example, during implantation.

A further non-limiting example of a lead 66 is a double helix lead enclosed in a sheath. The construction of the double helix, the anchor and other parts is similar to the lead described by Memberg et al. (1994). Memberg et al. (1994) describe a lead including a double helix enclosed in a sheath. The double helix is separated and the non-insulated wires are wound back on the stimulating end to which an anchor is attached. Similarly, an electrode without an anchor may serve as a single pick-up end electrode. For the purposes of the present invention, the lead of Memberg et al. (1994) has been modified. At the pick-up end 26, the double helix is separated and the wires wound back, forming two separate conductive pick-up electrodes 68. Similarly, at the stimulating end 28, the double helix is separated and the wires are wound back, forming two separate conductive stimulating electrodes 70. Alternatively, the double helix is separated and the wires are wound back separately to form two separate conductive pick-up electrodes 68 and two separate conductive stimulating electrodes 70. Optionally, anchor-shaped tines can be formed at the stimulating end 28 to anchor the conductive stimulating electrodes 70 in position.

Alternatively, commercially available multiple electrodes leads 66 can be connected via matching connectors to the array of conductive pick-up electrodes 68. Non-limiting examples include Axxess 3/6 lead (Advanced Neuromodulation Systems Inc., USA) or TO type lead (Dr. Osypka, GmbH Medizintechnik, Germany).

Figure 16A:
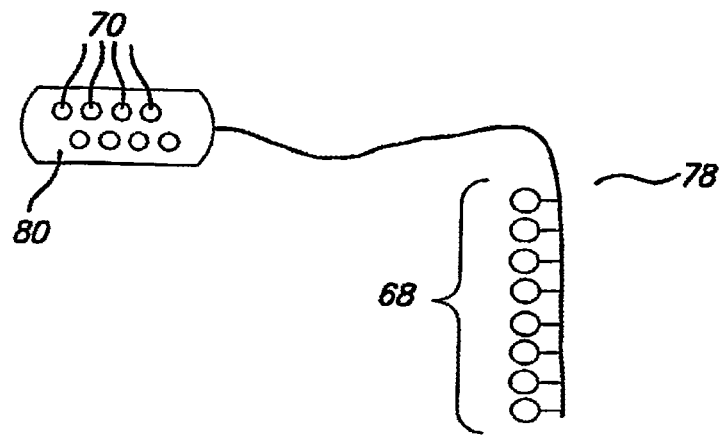
FIG. 16A is a schematic plan view illustrating a "paddle type" electrode having a paddle with conductive stimulating electrodes and disc-shaped conductive pick-up electrodes, arranged in a line.
Figure 16B:
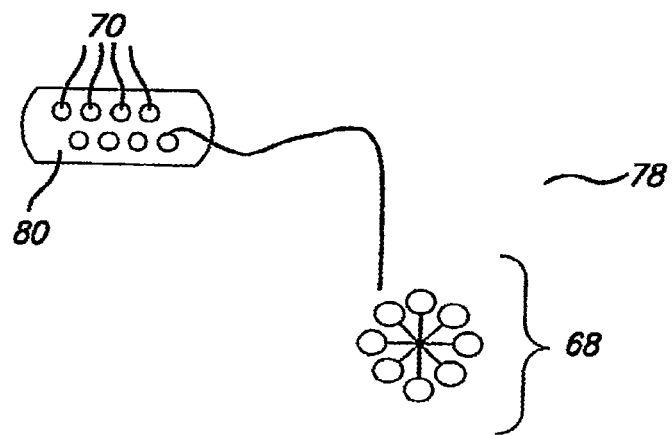
FIG. 16B is a schematic plan view illustrating a "paddle type" electrode having a paddle with conductive stimulating electrodes and disc-shaped conductive pick-up electrodes, arranged as a cluster.

An implant including a plurality of conductive stimulating electrodes 70 arranged as a cluster on a non-conductive substrate, a lead 66, and a plurality of conductive pick up electrodes 68 arranged either in a line or as a cluster can be used. For example, FIGS. 16A and 16B show a "paddle type" electrode 78 incorporating both conductive pick-up and stimulating electrodes 68, 70. FIG. 16A illustrates a "paddle type" electrode 78 having a paddle 80 with conductive stimulating electrodes 70, and disc-shaped conductive pick-up electrodes 68 arranged in a line. FIG. 16B illustrates a "paddle type" electrode 78 having disc-shaped conductive pick up electrodes 68 arranged as a cluster. The advantages of specific arrangement depends on the size and the shape of the area that should be covered by the electrodes.

Figure 17A:
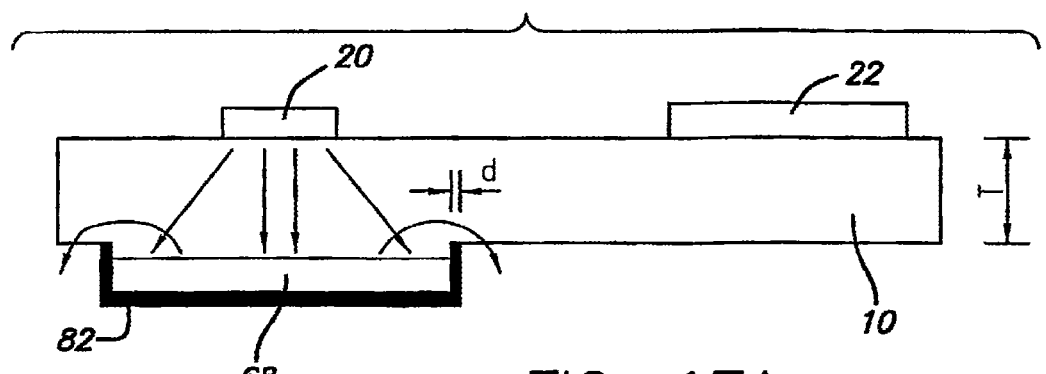
FIGS. 17A and 17B are schematic sectional views illustrating a conductive pick-up electrode with insulating material implanted subcutaneously.
Figure 17B:
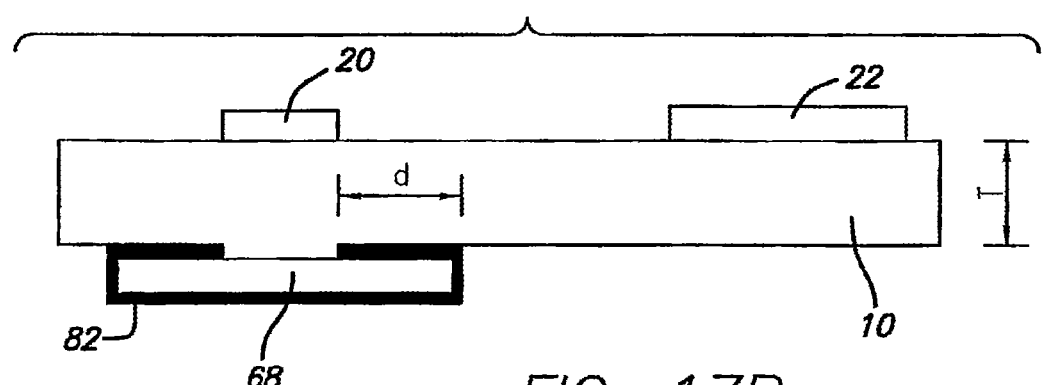

Optionally, a conductive pick-up electrode 68 with insulating material 82 covering its surface and periphery is beneficial. Electrical current from the surface cathodic electrode 20 may "escape" (escaping current designated as "Iescape") from the periphery of the conductive pick-up electrode 68 into the tissue (FIG. 17A). The path of this electrical current through the skin 10 may be short (indicated as "d"); thus, the resistance of the path may be small. It is known that the larger the diameter of the conductive pick-up electrode 68, the larger the peripheral area. This phenomenon acts against and may neutralize improved transcutaneous delivery for the larger diameter of the conductive pick-up electrode 68. In order to attenuate "Iescape," insulating material 82 is can be applied to cover the periphery of the conductive pick-up electrode 68 to cover the distance similar to the thickness of the skin 10 (FIG. 17B). Alternatively, insulating material 82 can be positioned below and extended beyond the conductive pick-up electrode 68. Suitable insulating material 82 can include, for example, silicone, polyester fiber such as Dacron™ (Invista, Inc) or other appropriate biocompatible materials. In this arrangement, the surface cathodic electrode 20 is preferably at least 10 mm in diameter. The conductive pick-up electrode 68 is preferably at least 16 mm in diameter. The conductive pick-up electrode 68 is covered with for example, at least 3 mm of insulating material 82 on its periphery.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All references cited in the present application are incorporated in their entirety by reference to the extent not inconsistent herewith.

REFERENCES

Gan, L., Bornes, T., Denington, A. and Prochazka, A. (2005) The stimulus router: a novel means of directing current from surface electrodes to nerves. IFESS 2005 Conference Proceedings, pp. 21-23.

Memberg W. D., Peckham P. H, Keith M. W. (June 1994) A surgically implanted intramuscular electrode for an implantable neuromuscular stimulation system. IEEE Transactions on Rehabilitation Engineering 2(2): 80-91.

Prochazka, A. (2004) Neural Prosthesis Program Meeting, NIH Meeting, November 2004.

PATENT DOCUMENTS

Gaunt, R. A. and Prochazka, A. Method of routing electrical current to bodily tissues via implanted passive conductors. U.S. patent application Ser. No. 11/337,824, filed Jan. 23, 2006.

Prochazka, A., Wieler, M., Kenwell, Z. R., Gauthier, M. J. A. (1996) Garment for applying controlled electrical stimulation to restore motor function. U.S. Pat. No. 5,562,707, issued Oct. 8, 1996.

Prochazka, A. Method and apparatus for controlling a device or process with vibrations generated by tooth clicks. International Patent Application Publication No. WO 2004/034937, published Oct. 16, 2003.

Prochazka, A. Method of routing electrical current to bodily tissues via implanted passive conductors. International Publication No. WO 2005/070494 A1, published Aug. 4, 2005.

Prochazka, A. Method and apparatus for controlling a device or process with vibrations generated by tooth clicks. U.S. Pat. No. 6,961,623, issued Nov. 1, 2005.

What is claimed is:

1. An apparatus, comprising:
a passive electrical conductor having a first end portion and a second end portion, the first end portion including a stimulation electrode, the second end portion including a pick-up electrode, the passive electrical conductor configured to be disposed within a body such that the stimulation electrode is disposed adjacent a target tissue and the pick-up electrode is entirely beneath a surface of a skin; and
an insulation member coupled to the second end portion of the passive electrical conductor, the insulation member configured to define, at least in part, a current pathway within the body along which a portion of an electrical current flows between a surface electrode coupled to the surface of the skin and the pick-up electrode.

2. The apparatus of claim 1, wherein the passive electrical conductor is insulated between the first end portion and the second end portion.

3. The apparatus of claim 1, wherein the insulation member is constructed from any one of silicone and polyester.

4. The apparatus of claim 1, wherein the insulation member is configured to inhibit the flow of the electrical current through a portion of a subcutaneous tissue.

5. The apparatus of claim 1, wherein at least a portion of the insulation member is disposed between the pick-up electrode and the stimulation electrode.

6. The apparatus of claim 1, wherein at least a portion of the insulation member is disposed about a periphery of the pick-up electrode.

7. The apparatus of claim 1, wherein:
the pick-up electrode is a first pick-up electrode from a plurality of pick-up electrodes; and
the insulation member is configured to be movably coupled to the passive electrical conductor such that the insulation member can selectively cover a second pick-up electrode from the plurality of pick-up electrodes.

8. The apparatus of claim 1, wherein at least a portion of the pick-up electrode has a coil shape.

9. The apparatus of claim 1, wherein the stimulation electrode is a stimulation electrode from a plurality of stimulation electrodes.

10. The apparatus of claim 1, wherein a surface area of the stimulation electrode is less than approximately 50 square millimeters.

11. The apparatus of claim 1, wherein a surface area of the stimulation electrode is between approximately 10 square millimeters and approximately 50 square millimeters.

12. The apparatus of claim 1, wherein:
the pick-up electrode is a pick-up electrode from a plurality of pick-up electrodes; and
the stimulation electrode is a stimulation electrode from a plurality of stimulation electrodes, each stimulation electrode from the plurality of stimulation electrodes being electronically coupled to a corresponding pick-up electrode from the plurality of pick-up electrodes.

13. The apparatus of claim 1, further comprising:
an anchor coupled to the first end portion of the passive electrical conductor, the anchor configured to limit movement of the stimulation electrode relative to the target tissue when the passive electrical conductor is disposed within the body.

14. A method, comprising:
inserting a conductive member within a body such that a stimulating electrode disposed at a distal end portion of the conductive member is adjacent a target tissue within the body and a pick-up electrode disposed at a proximal end portion of the conductive member is beneath a surface of a skin of the body; and
moving at least a portion of an insulation member relative to the proximal end portion of the conductive member after the inserting.

15. The method of claim 14, wherein an exterior surface of the conductive member is insulated between the distal end portion and the proximal end portion.

16. The method of claim 14, wherein the moving includes sliding the portion of the insulation member about the pick-up electrode.

17. The method of claim 14, wherein the moving includes defining at least a portion of a current pathway within the body between the surface of the skin and the pick-up electrode.

18. The method of claim 14, wherein the moving includes positioning at least the portion of the insulation member between the pick-up electrode the stimulation electrode.

19. The method of claim 14, further comprising:
coupling a surface electrode to the surface of the skin such that at least a portion of the pick-up electrode is below the surface electrode.

20. The method of claim 14, wherein the insulation member is coupled to the proximal end portion of the conductive member before the inserting.

* * * * *